United States Patent [19]

Collins et al.

[11] Patent Number: 5,780,600
[45] Date of Patent: Jul. 14, 1998

[54] PURIFIED CILIARY NEUROTROPHIC FACTOR

[75] Inventors: Franklin D. Collins; Leu-Fen Lin; Drzislav Mismer; Christine Ko, all of Boulder, Colo.

[73] Assignee: Amgen Inc., Thousand Oaks, Calif.

[21] Appl. No.: 448,909

[22] Filed: May 24, 1995

Related U.S. Application Data

[62] Division of Ser. No. 400,439, Mar. 2, 1995, which is a continuation of Ser. No. 76,282, Jun. 11, 1993, abandoned, which is a continuation of Ser. No. 857,544, Mar. 24, 1992, abandoned, which is a continuation of Ser. No. 458,564, Dec. 28, 1989, Pat. No. 5,141,856, and a continuation-in-part of Ser. No. 404,533, Sep. 8, 1989, Pat. No. 4,997,929, said Ser. No. 458,564, is a continuation-in-part of Ser. No. 293,851, Jan. 5, 1989, Pat. No. 5,011,914.

[51] Int. Cl.$^6$ .................................................. C07K 14/475
[52] U.S. Cl. ........................................ 530/399; 530/350
[58] Field of Search ................................ 530/350, 399, 530/412; 435/69.1

[56] References Cited

U.S. PATENT DOCUMENTS

| | | | |
|---|---|---|---|
| 4,399,216 | 8/1983 | Axel et al. | 435/6 |
| 4,923,696 | 5/1990 | Appel et al. | 424/548 |
| 4,997,929 | 3/1991 | Collins et al. | 536/27 |
| 5,011,914 | 4/1991 | Collins et al. | 530/399 |
| 5,028,622 | 7/1991 | Plaitakis | 514/561 |
| 5,141,856 | 8/1992 | Collins et al. | 435/69.1 |
| 5,349,056 | 9/1994 | Panayotatos | 530/399 |

FOREIGN PATENT DOCUMENTS

| | | |
|---|---|---|
| 911867 | of 0000 | Norway . |
| WO88/08848 | 11/1988 | WIPO . |
| WO09/10647 | 9/1990 | WIPO . |
| WO91/04316 | 4/1991 | WIPO . |

OTHER PUBLICATIONS

Manthorpe et al. (1986), Brain Research, 367:282–286.
Barbin et al. (1984), J. Neurochem., 43(5):1468–1478.
Watters et al. (1987), J. Neurochem., 49:705–713.
Heymanns et al. (1987), P.N.A.S., 84:7758–7762.
Hughes et al. (1988), Nature, 335:70–73.
Bonnerjea et al. (1986) Bio/Technology, 4:954–958.
Masu et al. (1993) Nature, 365:27–32.
Mitsumoto et al. (1994) Science, 265:1107–1108.
Nishi (1994) Science, 265:1052–1053.
Hofman (1988), J. Neurochem., 51:109–113.
Lillien et al. (1988), Neuron, 1:485–494.
Manthorpe et al. (1989) Nerve Growth Factors, Chapter 2, "Ciliary Neuronotrophic Factors", pp. 31–56, R.A. Rush (ed).
Saadat et al. (1989) Cell Biology, 108:1807–1816.
Harris et al. (1989) Protein Purification Methods: A Practical Approach, pp. 18–27, pp. 29–33, pp. 152–153, pp. 154–157, pp. 197–200, pp. 200–216, pp. 216–221, pp. 222–230, pp. 230–232, pp. 245–290 and pp. 293–306.
Scopes(1987) Protein Purification, Prinicipals and Practice, 2nd Ed., pp. 33–35, pp. 45–54, pp. 68–69, pp. 93–99, pp. 100–126, pp. 126–141, pp. 167–172, pp. 176–179, pp. 186–215, pp. 285–294, and 296–304.
Janson et al. (1989), Protein Purification: Principles, High Resolution, Methods and Application, pp. 15–16, pp. 63–106, pp. 107–148, pp. 149–174, pp. 175–206, pp. 207–226, pp. 275–329, pp. 364–366, pp. 439–442, pp. 376–403, pp. 433–439 and 404–427.
Barde et al. (1983), Ann. Rev. Physiol., 45:601–612.
Hofman et al. (1987), J. Neurochem., 48(5):1425–1433.
Collins et al. (1985), Developmental Biology, 109:255–258.
Watters et al. (1985), Biochem. Int. 11(2):245–253.
Lin et al. (1989), Science, 246(4933):1023–1025.
Lin et al. (1990), J. Biol. Chem., 265(15):8942–8947.
Mizrachi et al. (1986), J. Neurochem., 46(6):1675–1682.
Popiela et al. (1981), Developmental Biology, 83:266–277.
Bell et al. (1988), Proteins and Enzymes, pp. 32–34, 36.
Sofer et al. (1983), BioTechniques, 1(4):198–203.
Creighton (1984), Protein Structures and Molecular Properties, Freeman Co. (New York) pp. 39–42.
Kaufman et al. (1985) Molecular and Cellular Biology vol. 5 pp. 1750–1759.
Ringold et al. (1981) J. Mol. Apl. Genet. 1:165.
Lin et al. (1990) Chemical Abstract 112:69 No. 229805v.
Lin et al. (1990) Chemical Abstract 113:124 No. 18410v.
Maniatis et al. (1982) Molecular Cloning, A Laboratory Manual, Cold Spring Harbor Laboratory, CSH, New York pp. 405–450.
Appel (1981) Annals of Neurology 10:499–505.
Ebandal (1987) Chem. Abstr. 106:150248h.
Seidl et al. (1987) J. Neurochem. 49(1):169–174.

*Primary Examiner*—Marianne P. Allen
*Assistant Examiner*—Stephen Gucker
*Attorney, Agent, or Firm*—Nancy A. Oleski; Ron K. Levy; Steven M. Odre

[57] ABSTRACT

A ciliary neurotrophic factor (CNTF), particularly sciatic nerve CNTF (SN-CNTF) is claimed. The SN-CNTF described herein is a single protein species and has a specific activity that increased to greater than 25,000-fold from crude extract. Amino acid data for this SN-CNTF is also provided. In addition, methods for using this data for providing SN-CNTF probes and for screening cDNA and genomic libraries are also provided. Recombinant-DNA methods for the production of SN-CNTF are described. Nucleic acid sequences encoding rabbit and human CNTF are provided. A recombinant expression system is provided for producing biologically active CNTF.

9 Claims, 22 Drawing Sheets

↓ SAMPLE INJECTION
↦ START ELUTING WITH POLYBUFFER
— ABSORPTION AT 280 nm
○—○ pH
●—● CNTF ACTIVITY IN TU
⊢—⊣ FRACTIONS POOLED FOR FURTHER ANALYSIS

FIG. 11

```
G CAA ACT CAG CTG ACT TGT TTC CTG GGA CAG TTG AGT TAG GGG ATG GCT
                                                                M   A

TTC ATG GAG CAT TCA GCA CTG ACC CCT CAC CGC CGG GAG CTC TGT AGC
 F   M   E   H   S   A   L   T   P   H   R   R   E   L   C   S

CGT ACC ATC TGG CTA GCG AGG AAG ATT CGT TCA GAC CTG ACC GCT CTT
 R   T   I   W   L   A   R   K   I   R   S   D   L   T   A   L

ACG GAA TCT TAC GTG AAG CAT CAG GGC CTG AAC AAG AAC ATC AAC CTG
 T   E   S   Y   V   K   H   Q   G   L   N   K   N   I   N   L

GAC TCT GTG GAT GGA GTA CCA ATG GCA AGC ACT GAT CAG TGG AGT GAG
 D   S   V   D   G   V   P   M   A   S   T   D   Q   W   S   E

CTG ACT GAG GCA GAG CGA CTC CAA GAG AAC CTC CAA GCT TAT CGG ACC
 L   T   E   A   E   R   L   Q   E   N   L   Q   A   Y   R   T

TTC CAT ATT ATG TTG GCC AGG CTT TTA GAA GAC CAG CAG GTG CAT TTT
 F   H   I   M   L   A   R   L   L   E   D   Q   Q   V   H   F

ACC CCA GCT GAA GGT GAC TTC CAT CAA GCT ATA CAT ACC CTT TTA CTC
 T   P   A   E   G   D   F   H   Q   A   I   H   T   L   L   L

CAA GTT GCT GCC TTC GCT TAC CAG ATA GAG GAG TTA ATG GTG CTG TTG
 Q   V   A   A   F   A   Y   Q   I   E   E   L   M   V   L   L

GAA TGT AAT ATC CCT CCC AAA GAT GCT GAT GGG ACA CCT GTC ATT GGA
 E   C   N   I   P   P   K   D   A   D   G   T   P   V   I   G

GGT GAT GGT CTC TTT GAG AAG AAG CTG TGG GGC CTG AAG GTG CTA CAA
 G   D   G   L   F   E   K   K   L   W   G   L   K   V   L   Q

GAG CTT TCA CAC TGG ACA GTG AGA TCC ATT CAT GAC CTT CGT GTC ATT
 E   L   S   H   W   T   V   R   S   I   H   D   L   R   V   I

TCT TGT CAT CAA ACT GGA ATC CCA GCA CAT GGG AGC CAT TAT ATT GCT
 S   C   H   Q   T   G   I   P   A   H   G   S   H   Y   I   A

AAC GAC AAG GAA ATG TAG
 N   D   K   E   M
```

FIG. 12

```
                                              G                     TG
                                         ─────────────────────────────────
                                         TAA  GGG  ATG  GCT  TTC  ACA  GAG
                                              ─────────────────────────────
                                              met  ala  phe  thr  glu
                                                                   met G  A                         C         G              T A C
───────────────────────────────────────────────────────────────────────────
CAT  TCA  CCG  CTG  ACC  CCT  CAC  CGT  CGG  GAC  CTC  TGT  AGC  CGC  TCT  ATC  TGG
his  ser  pro  leu  thr  pro  his  arg  arg  asp  leu  cys  ser  arg  ser  ile  trp
          ala                              glu                   thr
   G                                         C                        T   C
───────────────────────────────────────────────────────────────────────────
CTA  GCA  AGG  AAG  ATT  CGT  TCA  GAC  CTG  ACT  GCT  CTT  ACG  GAA  TCC  TAT  GTG
leu  ala  arg  lys  ile  arg  ser  asp  leu  thr  ala  leu  thr  glu  ser  tyr  val T              A G A
───────────────────────────────────────────────────────────────────────────
AAG  CAT  CAG  GGC  CTG  AAC  AAG  AAC  ATC  AAC  CTG  GAC  TCT  GCG  GAT  GGG  ATG
lys  his  gln  gly  leu  asn  lys  asn  ile  asn  leu  asp  ser  ala  asp  gly  met
                                                            val            val
      A                                         T
───────────────────────────────────────────────────────────────────────────
CCA  GTG  GCA  AGC  ACT  GAT  CAG  TGG  AGT  GAG  CTG  ACC  GAG  GCA  GAG  CGA  CTC
pro  val  ala  ser  thr  asp  gln  trp  ser  glu  leu  thr  glu  ala  glu  arg  leu
     met
            C                    G              A   A                      T
───────────────────────────────────────────────────────────────────────────
CAA  GAG  AAC  CTT  CAA  GCT  TAT  CGT  ACC  TTC  CAT  GTT  TTG  TTG  GCC  AGG  CTC
gln  glu  asn  leu  gln  ala  tyr  arg  thr  phe  his  val  leu  leu  ala  arg  leu
                                                        ile  met
                                         G  T
───────────────────────────────────────────────────────────────────────────
TTA  GAA  GAC  CAG  CAG  GTG  CAT  TTT  ACC  CCA  ACC  GAA  GGT  GAC  TTC  CAT  CAA
leu  glu  asp  gln  gln  val  his  phe  thr  pro  thr  glu  gly  asp  phe  his  gln
                                                 ala
                  T A           T                 C     T
───────────────────────────────────────────────────────────────────────────
GCT  ATA  CAT  ACC  CTT  CTT  CTC  CAA  GTC  GCT  GCC  TTT  GCA  TAC  CAG  ATA  GAG
ala  ile  his  thr  leu  leu  leu  gln  val  ala  ala  phe  ala  tyr  gln  ile  glu G G   G T         G T  T         T  C C   A   T
───────────────────────────────────────────────────────────────────────────
GAG  TTA  ATG  ATA  CTC  CTG  GAA  TAC  AAG  ATC  CCC  CGC  AAT  GAG  GCT  GAT  GGG
glu  leu  met  ile  leu  leu  glu  tyr  lys  ile  pro  arg  asn  glu  ala  asp  gly
          val                      cys  asn          pro  lys  asp
  CA     G C   ───                  G T   A
───────────────────────────────────────────────────────────────────────────
ATG  CCT  ATT  AAT  GTT  GGA  GAT  GGT  GGT  CTC  TTT  GAG  AAG  AAG  CTG  TGG  GGC
met  pro  ile  asn  val  gly  asp  gly  gly  leu  phe  glu  lys  lys  leu  trp  gly
          val  ───  ile       gly  asp
   G              A   A              C            G    A         T
───────────────────────────────────────────────────────────────────────────
CTA  AAG  GTG  CTG  CAG  GAG  CTT  TCA  CAG  TGG  ACA  GTA  AGG  TCC  ATC  CAT  GAC
leu  lys  val  leu  gln  glu  leu  ser  gln  trp  thr  val  arg  ser  ile  his  asp
                                             his
      G              G       A         A                A
───────────────────────────────────────────────────────────────────────────
CTT  CGT  TTC  ATT  TCT  TCT  CAT  CAG  ACT  GGG  ATC  CCA  GCA  CGT  GGG  AGC  CAT
leu  arg  phe  ile  ser  ser  his  gln  thr  gly  ile  pro  ala  arg  gly  ser  his
          val            cys                                            his
                     G         G
───────────────────────────────────────────
TAT  ATT  GCT  AAC  AAC  AAG  AAA  ATG  TAG
tyr  ile  ala  asn  asn  lys  lys  met
               asp       glu
```

FIG. 16

Oligonucleotide 1
(FOR DELETING INTRON)

OLIGO-1 5'-GAT GTT CTT GTT CAG GCC CTG ATG CTT CAC
ATA GGA TTC CGT AAG AGC AGT CAG GTC TGA ACG AAT CTT CC-3'

(TOP LINE COMPLEMENTARY TO 3' SIDE OF INTRON)
(BOTTOM LINE COMPLEMENTARY TO 5' SIDE OF INTRON)

Oligonucleotides 2 & 3
(FOR RECONSTRUCTING 5' END OF EXPRESSED DNA)

```
                  BamHI    TRANSLATIONAL COUPLER
OLIGO-2 5'-      GATC  CGATCTTGGAGGATGATTAA   ATG GCT TTC
OLIGO-3 3'-GCTAGAACCTCCTACTAATT               TAC CGA AAG
                                              met ala phe
```

```
                                                    Bgl II
ACT GAA CAC TCT CCG CTG ACC CCG CAC CGT CGA  GAT CTG
TGA CTT GTG AGA GGC GAC TGG GGC GTG GCA GCT  CTA GAC
thr glu his ser pro leu thr pro his arg arg asp leu
```

```
                                  Nhe I
TGC AGC CGC TCT ATC TGG              -3' OLIGO-2
ACG TCG GCG AGA TAG ACC  GATC        -5' OLIGO-3
cys ser arg ser ile trp leu
```

Oligonucleotide 4
(FOR INSERTING Spe I SITE)

```
                              CCT TCT (ORIGINAL GENOMIC CODONS)
OLIGO-4 5'- ATG TAG CAG TTA GTC  ACT AGT  CTC TTC CTT GCT-3'
            met STOP             Spe I
```

FIG. 17

```
OLIGO-5  5'-[BamHI]GATC CGA TCT TGG AGG ATG ATT AAA TGG CTT TCA CCG AAC ACT CCC CGC TGA
OLIGO-6  3'-          GCT AGA ACC TCC TAC TAA TTT ACC GAA AGT GGC TTG TGA GGG GCG ACT

CCC CGC ACC GTC GTG ACC TGT GCT CCC GTT CCA TCT GGC TGG CT-3' OLIGO-5
GGG GCG TGG CAG CAC TGG ACA CGA GGG CAA      -5' OLIGO-6
```

```
OLIGO-7  5'- C GTA AAA TCC GTT CCG ACC TGA CCG CTC TGA CCG AAT
OLIGO-8  3'- GGT AGA CCG ACC GAG CAT TTT AGG CAA GGC TGG ACT GGC TTA

CCT ACG TTA AAC ACC AGG GTC TGA ACA AAA ACA TCA ACC TGG ACT CC-3' OLIGO-7
GGA TGC AAT TTG TGG TCC CAG ACT TGT TTT TGT AGT T-5' OLIGO-8
```

```
OLIGO-9   5'- G CTG ACG GTA TGC CGG TTG CTT CCA CCG ACC AGT GGT CCG
OLIGO-10  3'- GG ACC TGA GGC GAC TGC ACG GCC AAC GAA GGT GGC TGG TCA CCA GGC

AAC TGA CCG AAG CTG AAC GTC TGC AGG AAA ACC TGC A-3' OLIGO-9
TTG ACT GGC TTC GAC TTG CAG ACG TCC TTT TGG ACG[TTCGA]-5' OLIGO-10
                                              Hind III
```

PURIFIED CILIARY NEUROTROPHIC FACTOR

This is a divisional of application Ser. No. 08/400,439 filed on Mar. 2, 1995 which is a continuation of Ser. No. 08/076,282 filed on 11 Jun. 1993, abandoned.

BACKGROUND OF THE INVENTION

The present invention relates to neurotrophic factors and ciliary neurotrophic factor (CNTF) in particular, as well as methods of purifying CNTF and producing recombinant CNTF.

Severe mental and physical disabilities result from the death of nerve or glial cells in the nervous system. The death of nerve or glial cells can be caused by neurodegenerative diseases such as Alzheimer's and Parkinson's diseases and multiple sclerosis, by the ischemia resulting from stroke, by a traumatic injury, or by the natural aging process.

Neurotrophic factors are a class of molecules that promote the survival and functional activity of nerve or glial cells. Evidence exists to suggest that neurotrophic factors will be useful as treatments to prevent nerve or glial cell death or malfunction resulting from the conditions enumerated above. Appel, 1981, Ann. Neurology 10:499.

The best characterized of such neurotrophic factors is nerve growth factor (NGF). NGF has been demonstrated to be a neurotrophic factor for the forebrain cholinergic nerve cells that die during Alzheimer's disease and with increasing age. The loss of these nerve cells is generally considered responsible for many of the cognitive deficits associated with Alzheimer's diseases and with advanced age.

Experiments in animals demonstrate that NGF prevents the death of forebrain cholinergic nerve cells after traumatic injury and that NGF can reverse cognitive losses that occur with aging. Hefti and Weiner, 1986, Ann. Neurology 20:275; Fischer et al, 1987, Nature, 329:65. These results suggest the potential clinical utility in humans of this neurotrophic factor in the treatment of cognitive losses resulting from the death of forebrain cholinergic nerve cells through disease, injury or aging.

A complication of the use of neurotrophic factors is their specificity for only those subpopulations of nerve cells which possess the correct membrane receptors. Most nerve cells in the body lack NGF receptors and are apparently unresponsive to this neurotrophic factor. It is, therefore, of critical importance to discover new neurotrophic factors that can support the survival of different types of nerve of glial cells than does NGF.

New neurotrophic factors have been searched for by their ability to support the survival in culture of nerve cells that are not responsive to NGF. One widely used screening assay is designed to discover factors that promote the survival of ciliary ganglionic motor neurons that innervate skeletal and smooth muscle. These ciliary ganglionic nerve cell belong to the parasympathetic nervous system and their survival is not supported by NGF.

The presence of factors which promote the survival of ciliary ganglionic nerve cells have been reported from a variety of tissues and species. Many of these ciliary ganglionic neurotrophic activities have the following similar chemical and biological properties: (1) the activity is present in high concentration in sciatic nerves; (2) the neurotrophic activity survives exposure to the ionic detergent sodium dodecyl sulfate (SDS) and to the reducing agents beta-mercaptoethanol (BME) or dithiothreitol (DTT) during electrophoresis on SDS polyacrylamide reducing gels; and (3) on such gels the activity migrates with an apparent molecular weight between 24–28 kd. Collins, 1985, Developmental Biology, 109:255–258; Manthrope et al., 1986, Brain Research, 367:282–186.

Based on these similar properties, it has been proposed that the same or closely related molecules, typically referred to as "ciliary neurotrophic factor" or "CNTF", are responsible for the ciliary ganglionic neurotrophic activities. Thus, the term CNTF is an operational definition referring to agents with the above properties that promote the survival of ciliary ganglionic nerve cells in culture. Without sufficient data to establish that the proteins responsible for these activities are identical, CNTFs will be distinguished by their tissue and species of origin. Thus, if the species of origin is rabbit, the nomenclature is rabbit sciatic nerve CNTF (rabbit SN-CNTF).

Sciatic nerve CNTF is apparently found in highest concentration in peripheral nerves, such as the sciatic nerve. It is released from cells in the nerve upon injury. SN-CNTF supports the survival and growth of all peripheral nervous system nerve cells tested, including sensory, sympathetic, and parasympathetic nerve cells. Thus, SN-CNTF has a broader range of responsive nerve cells than does NGF. A rat SN-CNTF has recently been shown to regulate the formation of specific types of glial cells in the central nervous system (Hughes et al., 1988, Nature 335:70).

The most reasonable hypothesis based on the evidence cited above is that sciatic nerve CNTF is a component of the response of the nervous system to injury. SN-CNTF released from cells in a damaged nerve would be expected to promote the survival and regrowth of injured nerve cells and regulate the functional activation of glial cells necessary for regeneration. These considerations indicate that SN-CNTF would have therapeutic value in reducing damage to the nervous system caused by disease or injury.

Despite widespread scientific interest in SN-CNTF, the difficulty of purifying substantially amounts from natural sources and the unavailability of human SN-CNTF have hampered attempts to demonstrate its value in sustaining the viability of nerve cells during disease or after injury. Prior attempts to purify a rat SN-CNTF has resulted in an 800-fold enrichment over crude nerve extract in terms of specific activity. Manthorpe et al., 1986, Brain Research 367:282–286.

However, an eight hundred-fold increase in specific activity was insufficient to produce a single protein species. Therefore, the product showing increased activity obtained from the method described by Manthrope et al. is insufficient as it includes multiple protein species. It would be desirable to achieve a purification of SN-CNTF such that a single protein species is obtained with the appropriate biological activity. Once a single protein species is obtained, sequencing data obtained will be more accurate. By "single protein species," as that term is used hereafter in this specification and the appended claims, is meant a polypeptide or series of polypeptides with the same amino acid sequence throughout their active sites. In other words, if the operative portion of the amino acid sequence is the same between two or more polypeptides, they are "a single protein species" as defined herein even if there are minor heterogeneities with respect to length or charge.

SUMMARY OF THE INVENTION

An object of the present invention is to provide an improved method of purifying SN-CNTF.

Another object of the present invention is to provide a SN-CNTF purified to an extent greater than ever achieved before, such that a single protein species is obtained.

Yet another object of the present invention is to provide probes which facilitate screen of cDNA and genomic libraries in order to clone the animal and human genes encoding SN-CNTF.

Another object of the invention is to provide the nucleic acid and corresponding amino acid sequences for animal and human CNTF.

Another object of the invention is to provide recombinant expression systems in which the nucleic acid sequence for human or animal CNTF can be used to produce human or animal CNTF protein.

These and other objects are achieved by providing a method of purifying SN-CNTF such that specific activity is increased greater than 25,000-fold from crude extract to purified SN-CNTF. The SN-CNTF purified greater than 25,000-fold is also provided.

According to other preferred features of certain preferred embodiments of the present invention, SN-CNTF probes are provided for screening cDNA and genomic libraries for SN CNTF.

According to other preferred features of certain preferred embodiments of the present invention, rabbit and human amino acid and nucleic acid CNTF sequences are provided.

According to other preferred features of certain preferred embodiments of the present invention, a recombinant expression system is provided to produce biologically active animal or human CNTF.

According to other advantageous features of certain preferred embodiments of the present invention, a process of purifying SN-CNTF is provided which includes the steps of acid treatment, ammonium sulfate fractionation, chromatofocussing, running the preparation of SDS-Page gel and reverse phase-HPLC.

According to other advantageous features of certain preferred embodiments of the present invention, additional purification steps are provided in which hydrophobic interaction chromatography is used immediately before and after chromatofocussing.

It is to be understood that both the foregoing general description and the following detailed description are exemplary and explanatory only, and are not restrictive of the invention, as claimed. The accompanying drawings, which are incorporated in and constitute a part of the specification, illustrate various embodiments of the invention and, together with the description, serve to explain the principles of the invention.

BRIEF DESCRIPTION OF THE DRAWINGS

FIG. 11 depicts the nucleic acid sequence encoding for rabbit SN-CNTF. Translation of this nucleic acid sequence gives the corresponding amino acid sequence printed underneath in single letter code. Sequences that are underlined were confirmed by the amino acid sequence obtained from the SN-CNTF protein.

FIG. 12 depicts the nucleic acid and corresponding amino acid sequence (three letter code) for the coding sequence for human CNTF. The human sequences are between the lines. Where the rabbit nucleic acid or amino acid sequences differ from the human, they are written above and below the lines, respectively.

FIG. 16 depicts synthetic oligonucleotides 1 through 4 used in construction of CNTF-Sny1/3 and CNTF-Syn2/3.

FIG. 17 depicts synthetic oligonucleotides 5 through 10 used in construction of CNTF-Sny2/3.

DESCRIPTION OF THE PREFERRED EMBODIMENTS

Figure 1:
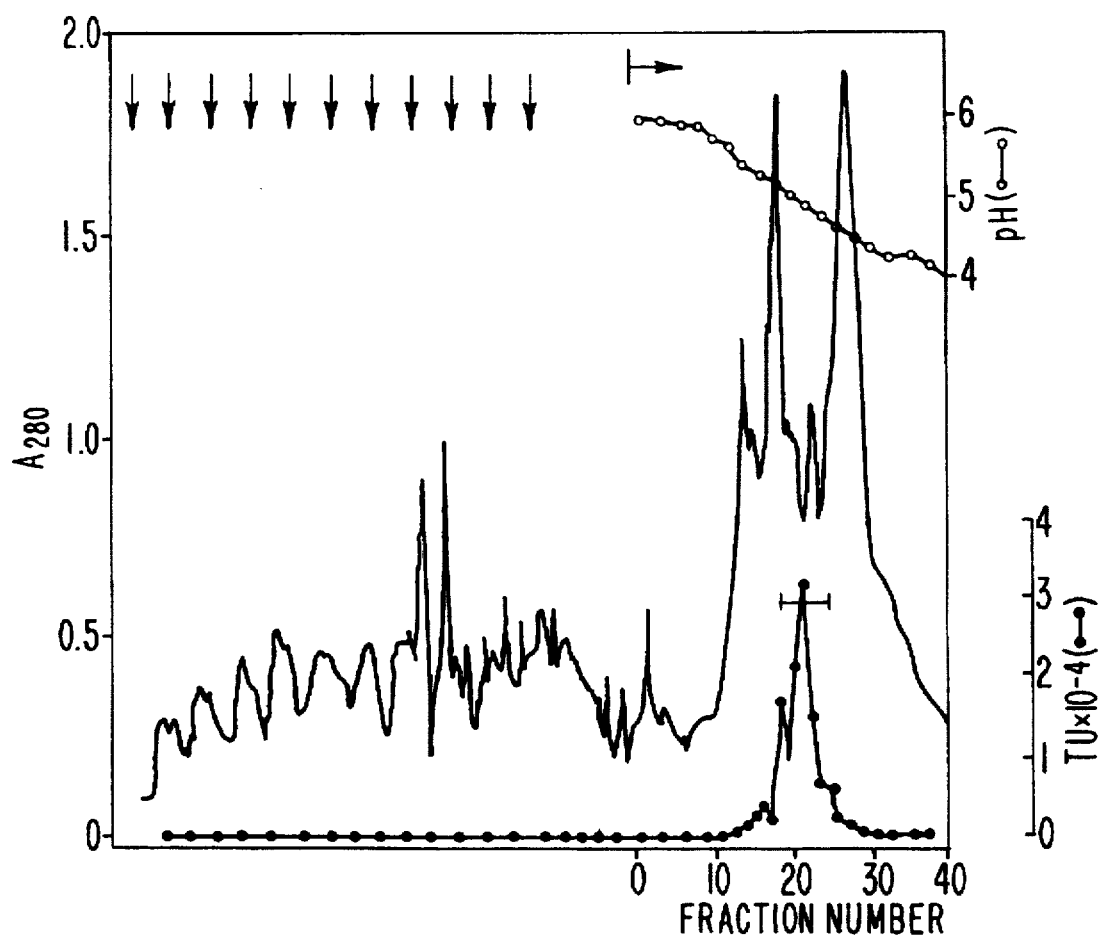
FIG. 1 depicts exemplary results of chromatography on a Mono P column.

Reference will now be made in detail to the presently preferred embodiments of the invention which, together with the following examples, serve to explain the principles of the invention.

As noted above, the present invention relates to an SN CNTF that is purified at least 25,000-fold from crude extract. This SN-CNTF is a single protein species as that term is defined herein. As a single protein species, the amino acid sequence of the SN-CNTF may be determined and used to design DNA probes for obtaining genomic or cDNA clones for use in recombinant production of SN-CNTF.

The amino acid sequence of the single protein species of SN-CNTF has been partially determined. That sequence is:

I — R — S — D — L — T — A — L — T — E — S —

Y — V — K — H — Q — G — L — N — K — N

D — G — V — P — M — A — G

K — L — W — G — L — K

Additional amino acid sequence has been determined from purified rabbit SN-CNTF which is given in Example 2. This additional sequence allows some of the amino acid sequence given above to be located within a single large peptide (Example 2). This single peptide sequence has been used to generate three degenerate oligonucleotide probes (#'s 1, 13, and 7 in Example 4) that are very useful for priming the polymerase chain reaction, since their position relative to each other is known.

The nucleic acid (mRNA equivalent) sequences encoding rabbit and human CNTF have been determined and are given in FIGS. 11 and 12.

A recombinant system for transiently expressing biologically active CNTF has been developed and is described in Example 5.

In addition, the present invention relates to an improved method of purifying SN-CNTF. While the present invention is related to SN-CNTF from any source, the description which follows will address that isolated from rabbits.

Briefly, one preferred embodiment of the present method includes pulverizing rabbit sciatic nerve material. The crude extract is then centrifuged. The supernatant is acidified and the resulting precipitate is removed by centrifugation. The supernatant is then titrated with NaOH and the resulting precipitate is again removed by centrifugation.

After pH precipitations, saturated ammonium sulfate solution is added to the supernatant and the precipitant is removed by centrifugation. With the further addition of ammonium sulfate to the supernatant, a precipitation of protein fraction containing most of the SN-CNTF activity results.

The above preparation is then loaded onto a Mono P chromatofocussing FPLC column. Column fractions are then collected and analysed for pH and CNTF activity. The fractions indicated by a bar in FIG. 1 with peak SN-CNTF activity is then further treated as will be discussed in detail below.

The focused fractions from multiple runs over the Mono P column are electrophoresed on SDS polyacrylamide slab gel. A region of the gel corresponding to molecular weights between 22 and 27 kd is cut across the width of the gel into multiple strips. The individual strips are cut into smaller pieces and proteins are eluted electrophoretically. Eluted proteins are collected, and the fraction with the highest activity is further purified using reverse-phase HPLC. This process is described in more detail in the Examples which follow.

In addition, the present invention relates to additional steps that can be inserted into the purification procedure given above in order to allow more starting material to be processed conveniently. In a preferred embodiment of these additional steps, hydrophobic interaction chromatography on phenyl-Sepharose is inserted between ammonium sulfate fractionation and chromatofocussing, while hydrophobic interaction chromatography on an FPLC alkyl-Superose column is inserted between chromatofocussing and preparative SDS-PAGE (Example 1).

The method provided by the present invention has resulted in SN-CNTF in a purified form with a greater than 25,000-fold increase in specific activity from the crude extract. Further, the final product produced is a single protein species. This represents an increase of greater than 30-fold over the SN-CNTF, which includes multiple protein species, reported as purified in Manthrope et al. discussed above. Since SN-CNTF is partially inactivated on reverse phase HPLC, the calculation of at least 25,000-fold purification according to the present invention represents a minimum purification, and the actual purification may be even 100,000-fold or greater. This increased purification will facilitate the determination of the amino acid sequence of SN-CNTF. According to the present invention, sufficient amino acid sequence has already been obtained to generate oligonucleotide probes that will facilitate screening of cDNA and genomic libraries in order to clone the animal and human genes coding for SN-CNTF.

The methods provided by the present invention have resulted in the determination of the coding (mRNA equivalent) sequence for rabbit and human CNTF.

As will be discussed in greater detail below, these genes will in turn make possible large-scale production of (1) animal SN-CNTF suitable for studies of its ability to treat animal models of nervous system damage, and (2) human SN-CNTF suitable for inclusion in pharmaceutical formulations useful in treating damage to the human nervous system.

The methods provided by the present invention have resulted in the production of biologically active animal CNTF in a recombinant expression system.

With these purified products, the amino acid sequence of the prominent peptides can be determined. The proteins are first treated with endoprotease Asp-N, endoprotease Lys-C endoprotease Glu-C, or chymotrypsin. After digestion, the amino acid sequence of prominent peptides can be determined using an Applied Biosystems gas phase protein sequencer.

Antibodies that react with purified SN-CNTF can be used for screening expression libraries in order to obtain the gene which encodes SN-CNTF. Synthetic peptides can be synthesized which correspond to regions of the sequence of SN-CNTF using an Applied Biosystems automated protein synthesizer. Such peptides can be used to prepare the antibodies. Antibodies to synthetic peptides have been produced and shown to react with purified CNTF by Western blot analysis (FIG. 10).

From the work above, an ultimate goal is to clone and express the human SN-CNTF gene in order to prepare material suitable for use in human pharmaceutical preparations. Once the genomic sequence is known, genes encoding SN-CNTF can then be expressed in animal or bacterial cells. The rabbit and human gene sequences encoding CNTF have been determined. A transient expression system for producing biologically active CNTF has been developed.

A recombinant DNA method for the manufacture of CNTF is now disclosed. In one embodiment of the invention, the active site functions in a manner biologically equivalent to that of the native CNTF isolated from human. A natural or synthetic DNA sequence may be used to direct production of the CNTF. This method comprises:

(a) Preparation of a DNA sequence capable of directing a host cell to produce a protein having CNTF activity;

(b) Cloning the DNA sequence into a vector capable of being transferred into and replicated in a host cell, such vector containing operational elements needed to express the DNA sequence;

(c) Transferring the vector containing the synthetic DNA sequence and operational elements into a host cell capable of expressing the DNA encoding CNTF;

(d) Culturing the host cells under conditions appropriate for amplification of the vector and expression of CNTF;

(e) Harvesting the CNTF; and (f) Permitting the CNTF to assume an active tertiary structure whereby it possesses CNTF activity.

In one embodiment, a partially or wholly synthetic DNA sequence used for production of recombinant CNTF may contain different nucleotides than the native DNA sequence. In a preferred embodiment, the DNA sequence with different nucleotides will still encode a polypeptide with the same primary structure as CNTF encoded by animal or human CNTF genes. In an alternate preferred embodiment, the DNA sequence with different nucleotides will encode a polypeptide with a primary structure related to natural CNTF and which has at least one of the biological activity of the CNTF described herein.

In one embodiment of the present invention, the native DNA sequence encoding CNTF is modified to promote expression in a host organism or cell. Such modifications may include the following:

(a) If the native DNA sequence is genomic DNA, the removal of intervening, non-coding sequences (introns) may be employed when expression in microorganisms is contemplated.

(b) Altering the nucleic acid sequence to include sequences recognized by various restrictions enzymes for ease of subsequent steps of ligation, cloning, and mutagensis.

(c) Altering the nucleic acid sequence to create codons preferred by the host organism or cell used to produce the recombinant protein.

(d) Linking the nucleic acid sequences to operational elements necessary to maintain and express the DNA in a host organism or cell.

In one embodiment of the present invention, the DNA sequence to be expressed is prepared as discussed above and inserted into an expression vector capable of residing in a host organism or cell and directing the expression of CNTF. Such vectors have certain preferred features suited for expression in a particular host organism or cell:

(a) Microorganism, especially *E. coli*

The vectors contemplated for use in the present invention include any vectors into which a DNA sequence as discussed above can be inserted, along with any preferred or required operational elements, and which vector can then be subsequently transferred into a host cell and replicated in such cell. Preferred vectors are those whose restriction sites have been well documented and which contain the operational elements preferred or required for transcription of the DNA sequence. However, certain embodiments of the present invention are also envisioned which employ currently undiscovered vectors which would contain one or more of the DNA sequences described herein. In particular, it is preferred that all of these vectors have some or all of the following characteristics: (1) possess a minimal number of host-organisms sequences; (2) be stably maintained an propagated in the desired host; (3) be capable of being present in a high copy number in the desired host; (4) possess a regulatable promoter positioned so as to promote transcription of the gene of interest; (5) have at least one marker DNA sequence coding for a selectable trait present on a portion of the plasmid separate from that where the DNA sequence will be inserted; and (6) a DNA sequence capable of terminating transcription.

In various preferred embodiments, there cloning vectors containing and capable of expressing the DNA sequences of the present invention contain various operational elements. These "operational elements," as discussed herein, include at least one promoter, at least one Shine-Dalgarno sequence and initiator codon, and at least one terminator codon. Preferably, these "operational elements" may also include one or more of the following: at least one operator, at least one leader sequence for proteins to be exported from intracellular space, at least one gene for a regulator protein, and any other DNA sequences necessary or preferred for appropriate transcription and subsequence translation of the vector DNA.

Certain of these operational elements may be present in each of the preferred vectors of the present invention. It is contemplated that any additional operational elements which may be required may be added to these vectors using methods known to those of ordinary skill in the art, particularly in light of the teachings herein.

In practice, it is possible to construct each of these vectors in a way that allows them to be easily isolated, assembled and interchanged. This facilitates assembly of numerous functional genes from combinations of these elements and the coding region of the DNA sequences. Further, many of these elements will be applicable in more than one host. It is additionally contemplated that the vectors, in certain preferred embodiments, will contain DNA sequences capable of functioning as regulators ("operators"), and other DNA sequences capable of coding for regulator proteins.

(i) Regulators

These regulators, in one embodiment, will serve to prevent expression of the DNA sequence in the presence of certain environmental conditions and, in the presence of other environmental conditions, will allow transcription and subsequent expression of the protein coded for by the DNA sequence. In particular, it is preferred that regulatory segments be inserted into the vector such that expression of the DNA sequence will not occur, or will occur to a greatly reduced extent, in the absence of, for example, isopropylthio-beta-D-galactoside (IPTG). In this situation, the transformed microorganism containing the DNA sequence may be grown to at a desired density prior to initiation of the expression of CNTF. In this embodiment, expression of the desired protein is induced by addition of a substance to the microbial environment capable of causing expression of the DNA sequence after the desired density has been achieved.

(ii) Promoters

The expression vectors must contain promoters which can be used by the host organism for expression of its own proteins. While the lactose promoter system is commonly used, other microbial promoters have been isolated and characterized, enabling one skilled in the art to use them for expression of the recombinant CNTF.

(iii) Transcription Terminator

The transcription terminators contemplated herein serve to stabilize the vector. In particular, those sequences as described by Rosenberg, M. and Court, D., in Ann. Rev. Genet. 13:319–353 (1979), specifically incorporated herein by reference, are contemplated for use in the present invention.

(iv) Non-Translated Sequence

It is noted that, in the preferred embodiment, it may also be desirable to reconstruct the 3' or 5' end of the coding region to allow incorporation of 3' or 5' non-translated sequences into the gene transcript. Included among these non-translated sequences are those which stabilize the mRNA as they are identified by Schmeissner, U., McKenney, K., Rosenberg, M and Court, D. in J. Mol. Biol. 176:39–53 (1984), specifically incorporated herein by reference.

(v) Ribosome Binding Sites

The microbial expression of foreign proteins requires certain operational elements which include, but are not limited to, ribosome binding sites. A ribosome binding site is a sequence which a ribosome recognizes and binds to in the initiation of protein synthesis as set forth in Bold, L., et al., Ann. Rev. Microbio. 35:557–580; or Marquis, D. M., et al., Gene 42:175–183 (1986), both of which are specifically incorporated herein by reference. A preferred ribosome binding site is GAGGCGCAAAAA(ATG).

(vi) Leader Sequence and Translational Coupler

Additionally, it is preferred that DNA coding for an appropriate secretory leader (signal) sequence be present at the 5' end of the DNA sequence as set forth by Watson, M. E. in Nucleic Acids Res. 12:5145–5163, specifically incorporated herein by reference, if the protein is to be excreted from the cytoplasm. The DNA for the leader sequence must be in a position which allows the production of a fusion protein in which the leader sequence is immediately adjacent to and covalently joined to CNTF, i.e., there must be no transcription or translation termination signals between the two DNA coding sequences. The presence of the leader sequence is desired in part for one or more of the following reasons. First, the presence of the leader sequence may facilitate host processing of CNTF. In particular, the leader sequence may direct cleavage of the initial translation product by a leader peptidase to remove the leader sequence and leave a polypeptide with the amino acid sequence which has potential protein activity. Second, the presence of the leader sequence may facilitate purification of CNTF through directing the protein out of the cell cytoplasm. In some species of host microorganisms, the presence of an appropriate leader sequence will allow transport of the completed protein into the periplasmic space, as in the case of some *E. coli*. In the case of certain *E. coli*, Saccharomyces and strains of Bacillus and Pseudomonas, the appropriate leader sequence will allow transport of the protein through the cell membrane and into the extracellular medium. In this situation, the protein may be purified from extracellular protein. Thirdly, in the case of some of the proteins prepared by the present invention, the presence of the leader sequence may be necessary to locate the completely protein in an environment where it may fold to assume its active structure, which structure possesses the appropriate protein activity.

In one preferred embodiment of the present invention, an additional DNA sequence is located immediately preceding the DNA sequence which codes for CNTF. The additional DNA sequence is capable of functioning as a translational coupler, i.e., it is a DNA sequence that encodes an RNA which services to position ribosomes immediately adjacent to the ribosome binding site of the inhibitor RNA with which it is contiguous. In one embodiment of the present invention, the translational coupler may be derived using the DNA sequence TAACGAGGCGCAAAAAATGAAAAAGA-CAGCTATCGCGATCTTGGAGGATGATTAAATG and method currently known to those of ordinary skill in the art related to translational couplers.

(vii) Translational Terminator

The translation terminators contemplated herein serve to stop the translation of mRNA. They may be either natural, as described by Kohli, J., Mol. Gen. Genet. 182:430–439; or synthesized, as described by Patterson, R. F. Gene 24:15–27 (1983), both of which references are specifically incorporated herein by reference.

(viii) Selectable Marker

Additionally, it is preferred that the cloning vector contain a selectable marker, such as a drug resistance marker or other marker which causes expression of a selectable trait by the host microorganism. In one embodiment of the present invention, the gene for amplicillin resistance is included in the vector while, in other plasmids, the gene for tetracycline resistance or the gene for chloramphenicol resistance is included.

Such a drug resistance or other selectable marker is intended in part to facilitate in the selection of transformants. Additionally, the presence of such a selectable marker in the cloning vector may be of use in keeping contaminating microroorgansims from multiplying in the culture medium. In this embodiment, a pure culture of the transformed host microorgansims would be obtained by culturing the microorganisms under conditions which require the induced phenotype for survival.

The operational elements as discussed herein are routinely selected by those of ordinary skill in the art in light of prior literature and the teachings contained herein. General examples of these operational elements are set forth in B. Lewin, *Genes*, Wiley & Sons, New York (1983), which is specifically incorporated herein by reference. Various examples of suitable operational elements may be found on the vectors discussed above and may be elucidated through review of the publications discussing the basic characteristics of the aforementioned vectors.

Upon synthesis and isolation of all necessary and desired component parts of the above-discussed vector, the vector is assembled by methods generally known to those of ordinary skill in the art. Assembly of such vectors is believed to be within the duties and tasks performed by those with ordinary skill in the art and as such, is capable of being performed without undue experimentation. For example, similar DNA sequences have been ligated into appropriate cloning vectors, as set forth by Maniatis et al. in Molecular Cloning, Cold Spring Harbor Laboratories (1984), which is specifically incorporated herein by reference.

In construction of the cloning vectors of the present invention, it should be additionally be noted that multiple copies of the DNA sequence and its attendant operational elements may be inserted into each vector. In such an embodiment, the host organism would produce greater amounts per vector of the desired CNTF. The number of multiple copies of the DNA sequence which may be inserted into the vector is limited only by the ability of the resultant vector, due to its size, to be transferred into and replicated and transcribed in an appropriate host cell.

(b) Other Microorganisms

Vectors suitable for use in microorganisms other than *E. coli* are also contemplated for this invention. Such vectors are described in Table 1. In addition, certain preferred vectors are discussed below.

11. Koshland, D. and Botstein, D. Cell 20, 749–760 (1980).

12. Movva, N. R., Kakamura, K. and Inouye, M. J. Mol. Biol. 143, 317–328 (1980).

13. Surin, B. P., Jans, D. A., Fimmel, A. L., Shaw, D. C., Cox, G. B. and Rosenberg, H. J. Bacteriol. 157, 772–778 (1984).

14. Sutcliffe, J. G. Proc. Natl. Acad. Sci. U.S.A. 75, 3737–3741 (1978).

15. Peden, K. W. C. Gene 22, 277–280 (1983).

16. Alton, N. K. and Vapnek, D. Nature 282, 864–869 (1979).

17. Yang, M., Galizzi, A., and Henner, D. Nuc. Acids Res. 237–248 (1983).

TABLE 1

| HOST | REGULATED PROMOTERS | INDUCER | TRANS-CRIPTION TERMINATOR | MHNA STABIL-IZATION | TRANSCRIP-TIONAL START SITE & LEADER PEPTIDE | MARKER | RS BINDING SITE |
|---|---|---|---|---|---|---|---|
| E. coli | Lac[1], Tac[2] Lambda pt. Trp[5] | IPTG increased temperature IAA addition or tryptophan depletion | rrnB[6] rrnC[7] | ompA[8] lambda int[9] trp[10] | bla[11] ompA[12] phoS | ampicillin[14] tetra-cycline[14,15] chloram-phenical[16] | |
| Bacillus | *alpha amylase[17] *sub-tilison[18] *p-43[19] spac-1[26] | IPTG | E. coli rrn rrn BT.T[20] | | B. amy neutral protease[21] B. amy alpha-amylase[22] B. subt. subtilisin[23] | Kan[r 24] Cam[r 25] | B. amy neural protease B. amy alpha amylase[22] |
| Pseudo-monas | Trp[27] (E. coli) Lac (E. coli) (E. coli) | IAA addition, or tryptophan depletion IPTG | | | phos-pholipase C[28] exotoxin A[29] | sulfon-amide[30] strep-tomycin[30] | Trp (E. coli) |
| Yeast | Gal 1[31], 10[32] Adl 1[33], 11[34] Pho 5 | Glucose depletion and galactose Glucose depletion Phosphate depletion | Cyc 1 Una Alpha Factor Sac 2 | | Invertase[36] Acid phos-phastase[36] Alpha Factor Factor | Ura 3[37] Leu 2[38] His 3 Tap 1 Tap 1 | |

*non regulated

1. Backman, K. Ptashne, M. and gilbert, W. Proc. Natl. Acad. Sci. U.S.A. 73, 4174–4178 (1976).

2. de Boer, H. A., Comstock, L. J., and Vasser, M. Proc. Natl. Acad. Sci. U.S.A. 80, 21–25 (1983).

3. Shimatake, H. and Rosenberg, M. Nature 292, 128–132 (1981).

4. Derome, C., Gheysen, D. and Fiers, W. Gene 17, 45–54 (1982).

5. Hallewell, R. A. and Emtage, S. Gene 9, 27–47 (1980).

6. Brosius, J., Dull, T. J., Sleeter, D. D. and Noller, H. F. J. Mol. Biol. 148, 107–127 (1981).

7. Normanly, J., Ogden, R. C., Horvath, S. J. and Abelson, J. Nature 321, 213–219 (1986).

8. Belasco, J. G., Nilsson, G., von Gabain, A. and Cohen, S. N. Cell 46, 245–251 (1986).

9. Schmeissner, U., McKenney, K., Rosenberg M. and Court, D. J. Mol. Biol. 176, 39–53 (1984).

10. Mott, J. E., Galloway, J. L. and Platt, T. EMBO J. 4, 1887–1891 (1985).

18. Wong, S.-L., Price C. W., Goldfarb, D. S., and Doi, R. H. Proc. Natl. Acad. Sci. U.S.A. 81, 1184–1188 (1984).

19. Wang, P.-Z., and Doi, R. H. J. Biol. Chem. 251, 8619–8625, (1984).

20. Lin, C.-K., Quinn, L. A. Rodriquez, R. L., J. Cell Biochem. Suppl. (9B), p. 198 (1985).

21. Vasantha, N., Thompson, L. D., Rhodes, C., Banner, C., Nagle, J., and Filpula, D. J. Bact. 159(3), 811–819 (1984).

22. Palva, I., Sarvas, M., Lehtovaara, P., Sibazkov, M., and Karriainen, L. Proc. Natl. Acad. Sci. U.S.A. 79, 5582–5586 (1982).

23. Wong, S.-L., Price, C. W., Goldfarb, D. S., and Doi, R. H. Proc. Natl. Acad. Sci. U.S.A. 81, 1184–1188 (1984).

24. Sullivan, M. A., Yasbin, R. E., and Young, F. E. Gene 29, 21–46 (1984).

25. Vasantha, N., Thompson, L. D., Rhodes, C., Banner, C., Nagle, J., and Filula, D. J. Bact. 159(3), 811–819 (1984).

26. Yansura, D. G. and Henner, D. J. PNAS 81, 439–443 (1984).
27. Gray, G. L., McKeown, K. A., Jones, A. J. S., Seeburg, P. H. and Heyneker, H. L. Biotechnology, 161–165 (1984).
28. Lory, S., and Tai, P. C. Gene 22, 95–101 (1983).
29. Liu, P. V. J. Infect. Dis. 130 (suppl), 594–599 (1974).
30. Wood, D. G. Hollinger, M. F., and Tindol, M. B. J. Bact. 145, 1448–1451 (1981).
31. St. John, T. P. and Davis, R. W. J. Mol. Biol. 152, 285–315 (1981).
32. Hopper, J. E., and Rowe, L. B. J. Biol. Chem. 253, 7566–7569 (1978).
33. Denis, C. L., Ferguson, J. and Young, E. T. J. Biol. Chem. 258–1165–1171 (1983).
34. Lutsdorf, L. and Megnet, R. Archs. Biochem. Biophys. 126, 933–944 (1968).
35. Meyhack, B., Bajwa, N., Rudolph, H. and Hinnen, a. EMBO J. 6, 675–680 (1982).
36. Watson, M. E. Nucleic Acid Research 12, 5145–5164 (1984).
37. Gerband, C. and Guerineau, M. Curr. Genet. 1, 219–228 (1980).
38. Hinnen, A., Hick, J. B. and Fink, G. R. Proc. Natl. Acad. Sci. U.S.A. 75, 1929–1933 (1978).
39. Jabbar, M. A., Sivasubramanian, N. and Nayak, D. P. Proc. Natl. Acad. Sci. U.S.A. 82, 2019–2023 (1985).

(i) Pseudomonas Vectors

Several vector plasmids which autonomously replicate in a broad range of Gram negative bacteria are preferred for use as cloning vehicles in hosts of the genus Pseudomonas. Certain of there are described by Tait, R. C., Close, T. J., Lundquist, R. C., Hagiya, M., Rodriguez, R. L., and Kado, C. I. In Biotechnology, May, 1983, pp. 269–275; Panopoulos, N. J. in *Genetic Engineering in the Plant Sciences*, Praeger Publishers, New York, N.Y., pp. 163–185 (1981); and Sakagucki, K. in Current Topic in Microbiology and Immunology 96:31–45 (1982), each of which is specifically incorporated herein by reference.

One particularly preferred construction would employ the plasmid RSF1010 and derivatives thereof as described by Bagdasarian, M., Bagdasarian, M. M., Coleman, S., and Timmis, K. N. in *Plasmids of Medical, Environmental and Commercial Importance*, Timmis, K. N. and Puhler, A. eds., Elsevier/North Holland Biomedical Press (1979), specifically incorporated herein by reference. The advantages of RSF1010 are that it is relatively a small, high copy number plasmid which is readily transformed into and stably maintained in both *E. coli* and Pseudomonas species. In this system, it would be preferred to use the Tac expression systems as described for Escherichia, since it appears that the *E. coli* trp promoter is readily recognized by Pseudomonas RNA polymerase as set forth by Sakagucki, K. in Current Topics in Microbiology and Immunology 96:31–45 (1982) and Gray, G. L., McKeown, K. A., Jones, A. J. S., Seeburg, P. H., and Heyneker, H. L. in Biotechnology, Feb. 1984, pp. 161–165, both of which are specifically incorporated herein by reference. Transcriptional activity may be further maximized by requiring the exchange of the promoter with, e.g., an *E. coli* or *P. aeruginosa* trp promoter. Additionally, the lacI gene of *E. coli* would also be included in the plasmid to effect regulation.

Translation may be coupled to translation initiation for any of the Pseudomonas proteins, as well as to initiation sites for any of the highly expressed proteins of the type chosen to cause intracellular expression of the inhibitor.

In those cases where restriction minus strains of a host Pseudomonas species are not available, transformation efficiency with plasmid constructs isolated from *E. coli* are poor. Therefore, passage of the Pseudomonas cloning vector through an r– m+ strain of another species prior to transformation of the desired host, as set forth in Bagdasarian, M., et a., *Plasmids of Medical, Environmental and Commercial Importance*, pp. 411–422, Timmis and Puhler eds., Elsevier/North Holland Biomedical Press (1979), specifically incorporated herein by reference, is desired.

(ii) Bacillus Vectors

Furthermore, a preferred expression system in hosts of the genus Bacillus involves using plasmid pUB110 as the cloning vehicle. As in other host vector system, it is possible in Bacillus to express the CNTF of the present invention as either an intracellular or a secreted protein. The present embodiments include both systems. Shuttle vectors that replicate in both Bacillus and *E. coli* are available for constructing and testing various genes as described by Dubnau, D., Gryczan, T., Contente, S., and Shivakumar, A. G. in *Genetic Engineering*, Vol. 2, Setlow and Hollander eds., Plenum Press, New York, N.Y., pp. 115–131 (1980) specifically incorporated herein by reference. For the expression and secretion of the CNTF from *B. subtilis*, the signal sequence of alpha-amylase is preferably coupled to the coding region for the protein. For synthesis of intracellular CNTF the portable DNA sequence will be translationally coupled to the ribosome binding site of the alpha-amylase leader sequence.

Transcription of either of these constructs is preferably directed by the alpha-amylase promoter or a derivative thereof. This derivative contains the RNA polymerase recognition sequence of the native alpha-amylase promoter but incorporates the lac operator region as well. Similar hybrid promoters constructed from the penicillinase gene promoter and the lac operator have been shown to function in Bacillus hosts in a regulatable fashion as set forth by Yansura, D. G. and Henner in *Genetics and Biotechnology of Bacilli*, Ganesan, A. T. and Hoch, J. A., eds., Academic Press, pp. 249–263 (1984), specifically incorporated by reference. The lacI gene of *E. coli* would also be included in the plasmid to effect regulation.

(iii) Clostridium Vectors

One preferred construction for expression in Clostridium is in plasmid pJU12, described by Squires, C. H. et al., in J. Bacteriol. 159:465–471 (1984) and specifically incorporated herein by reference, transformed into *C. perfringens* by the method of Heefner, D. L. et al., as described in J. Bacteriol. 159:460–464 (1984), specifically incorporated herein by reference. Transcription is directed by the promoter of the tetracycline resistance gene. Translation is coupled to the Shine-Dalgarno sequences of this same tet$^r$ gene in a manner strictly analogous to the procedures outlined above for vectors suitable for use in other hosts.

(iv) Yeast Vectors

Maintenance of foreign DNA introduced into yeast can be effected in several ways as described by Botstein, D. and Davis, R. W., in *The Molecular Biology of the Yeast Saccharomyces*, Cold Spring Harbor Laboratory, Strathern, Jones and Broach, eds., pp. 607–636 (1982), specifically incorporated hereby by reference. One preferred expression system for use with host organisms of the genus Saccharomyces harbors the CNTF gene of the 2 micron plasmid. The advantage of the 2 micron circle include relatively high copy number and stability when introduced into cir$^\circ$ strains. These vectors preferably incorporate the replication origin and at least one antibiotic resistance marker from pBR322 to allow replication and selection in *E. coli*. In addition, the plasmid will preferably have the two micron sequence and the yeast LEU2 gene to serve the same purpose in LEU2 defective mutants of yeast.

If it is contemplated that the recombinant CNTF will ultimately be expressed in yeast, it is preferred that the cloning vector first be transferred into *Escherichia coli*, where the vector would be allowed to replicate and from which the vector would be obtained and purified after amplification. The vector would then be transferred into the yeast for ultimate expression of CNTF.

(c) Mammalian Cells

The cDNA or genomic DNA encoding CNTF will serve as the gene for expression of CNTF in mammalian cells. It should have a sequence that will be efficient at binding ribsomes such as that described by Kozak, in Nucleic Acids Research 15:8125–8132 (1987), specifically incorporated herein by reference. The DNA restriction fragment carrying the DNA sequence encoding CNTF can be inserted into an expression vector which has a transcriptional promoter and a transcriptional enhancer as described by Guarente, L. in Cell 52:303–305 (1988) and Kadonage, J. T. et al., in Cell 51:1079–1090 (1987), both of which are specifically incorporated herein by reference. The promoter may be regulatable as in the plasmid pMSG (Pharmacia Cat. No. 27450601) if constitutive expression of the inhibitor is harmful to cell growth. The vector should have a complete polyadenylation signal as described by Ausubel, F. M. et al. in Current Protocols in Molecular Biology, Wiley (1987), specifically incorporated herein by reference, so that the mRNA transcribed from this vector is processed properly. Finally, the vector will have the replication origin and at least one antibiotic resistance marker from pBR322 to allow replication and selection of *E. coli*.

In order to select a stable cell line that produces CNTF, the expression vector can carry the gene for a selectable marker such as a drug resistance marker or carry a complementary gene for a deficient cell line, such as a dihydrofolate reductase (dhfr) gene for transforming a dhfr⁻ cell line as described in Ausubel et al., supra. Alternatively, a separate plasmid carrying the selectable marker can be cotransformed along with the expression vector.

Host Cells/Transformation

The vector thus obtained is transferred into an appropriate host cell. These host cells may be microorganisms or mammalian cells.

(a) Microorganisms

It is believed that any microorganism having the ability to take up exogenous DNA and express those genes and attendant operational elements may be chosen. After a host organism has been chosen, the vector is transferred into the host organism using methods generally known to those of ordinary skill in the art. Examples of such methods may be found in Advanced Bacterial Genetics by R. W. Davis et al., Cold Spring Harbor Press, Cold Spring Harbor, N.Y. (1980), which is specifically incorporated herein by reference. It is preferred, in one embodiment, that the transformation occur at low temperatures, as temperature regulation is contemplated has a means of regulating gene expression through the use of operational elements as set forth above. In another embodiment, if osmolar regulators have been inserted into the vector, regulation of the salt concentrations during the transformation would be required to insure appropriate control of the foreign genes.

It is preferred that the host microorganism would be a facultative anaerobe or an aerobe. Particular hosts which may be preferable for use in this method include yeasts and bacteria. Specific yeasts include those of the genus Saccharomyces, and especially *Saccharomyces cerevisiae*. Specific bacteria include those of the genera Bacillus, Escherichia, and Pseudomonas, especially *Bacillus subtilis* and *Escherichia coli*. Additional host cells are listed in Table I, supra.

(b) Mammalian Cells

The vector can be introduced into mammalian cells in culture by several techniques such as calcium phosphate:DNA coprecipitation, electroporation, or protoplast fusion. The preferred method is coprecipitation with calcium phosphate as described by Ausubel et al., supra.

Many stable cell types exist that are transformable and capable of transcribing processing, and translating the DNA sequence and producing CNTF protein. However, cell types may be variable with regard to glycosylation of proteins and post-translation modification of amino acid residues, if any. Thus, the ideal cell types are those that produce a recombinant CNTF identical to the natural molecule.

The host cells are cultured under conditions appropriate for the expression of CNTF. These conditions are generally specific for the host cell, and are readily determined by one of ordinary skill in the art in light of the published literature regarding the growth conditions for such cells and the teachings contained herein. For example, Bergey's Manual of Determinative Bacteriology, 8th Ed., Williams & Wilkins Company, Baltimore, Md., which is specifically incorporated herein by reference, contains information on conditions for culturing bacteria. Similar information on culturing yeast and mammalian cells may be obtained from Pollack, R. Mammalian Cell Culture, Cold Spring Harbor Laboratories (1975), specifically incorporated herein by reference.

Any conditions necessary for the regulation of the expression of the DNA sequence, dependent upon any operational elements inserted into or present in the vector, would be in effect at the transformation and culturing stages. In one embodiment, cells are grown to a high density in the presence of appropriate regulatory conditions which inhibit the expression of the DNA sequence. When optimal cell density is approached, the environmental conditions are altered to those appropriate for expression of the DNA sequence. It is thus contemplated that the production of CNTF will occur in a time span subsequent to the growth of the host cells to near optimal density, and that the resultant will be harvested at some time after the regulatory conditions necessary for its expression were induced.

In one embodiment of the present invention, recombinant CNTF will be purified after expression in a host cell or organism. In a preferred embodiment, recombinant CNTF will be purified after expression in microorganisms, particularly *E. coli*. In a preferred embodiment of the present invention, CNTF is present in its biologically active state upon recovery from the bacterial cultures. In an alternate preferred embodiment, CNTF may be allowed to re-fold to assume its active structure at a particular step in the purification process.

For purification of the recombinant protein, some combination of the following steps in preferably used: anion exchange chromatography (Mono-Q, Mono-S, and/or DEAE-Sepharose), gel permeation chromatography (Superose), chromatofocussing (Mono-P), and hydrophobic interaction chromatography (octyl- and/or phenyl-Sepharose).

It is to be understood that application of the teachings of the present invention to a specific problem or environment will be within the capabilities of one having ordinary skill in the art in light of the teachings contained herein.

The following examples are provided to illustrate certain preferred embodiments of the present invention, and are not restrictive of the invention, as claimed. All references provided in these Examples are specifically incorporated herein by reference.

EXAMPLE 1

Protein Preparation

Materials

Adult rabbit sciatic nerves were obtained from Pel-Freez Biologicals, Rogers, Ark. Ammonium sulfate (ultrapure) was purchased from Schwartz/Mann Biotech, Cleveland, Ohio. Phenylmethylsulfonyl fluoride (PMSF), epsilon-aminocaproic acid, benzamidine, pepstatin, dithiothreitol (DTT), poly-L ornithine (P3655), and 3-|4,5-dimethylthiazol-2 yl]-2,5-diphenyl-tetra-zolium bromide (MTT) were obtained from Sigma Chemical Co., St. Louis, Mo. Mono P chromatofocussing FPLC columns were obtained from Pharmacia, Inc., Piscataway, N.J. C8 reverse phase HPLC columns were obtained from Synchrom, Inc., Lafayette, Ind. Acetonitrile was purchased from J.T. Baker Chemical Co., Phillipsburg, N.J. Trifluoroacetic acid was obtained from Pierce Chemicals, Rockford, Ill. Endoproteases Asp-N and Lys-C were obtained from Boehringer Mannheim Biochemicals, Indianapolis, Ind. Fetal calf serum was purchased from Hyclone Laboratories, Logan, Utah. Culture media and salt solutions were obtained from Irvine Scientific, Santa Ana, Calif. Culture dishes were obtained from Costar, Cambridge, Mass. Utility grade pathogen-free fertile chick embryo eggs were obtained from Spafas, Roanoke, Ill.

B. Assay for SN-CNTF

Cultures of primary which embryo ciliary ganglia were prepared as previously described (Collins, 1978, Develop. Biol. 65:50; Manthorpe et al., 1986, Develop. Brain Res. 25:191). Briefly, ciliary ganglia were removed from fertile, pathogen free chicken eggs that had been incubated for 9–10 days at 38° C. in a humidified atmosphere. The ganglia were chemically dissociated by exposure first to Hanks' Balanced Salt Solution without divalent cations, containing 10 mM HEPES buffer pH 7.2 for 10 min at 37° C., and then by exposure to a solution of 0.125% bactotrypsin 1:250 (Difco, Detroit, Mich.) in Hanks' Balanced Salt Solution modified as above for 12 min at 37° C. Trypsinizaton was stopped by addition of fetal calf serum to a final concentration of 10%.

After this treatment, ganglia were transferred to a solution consisting of Dulbecco's high glucose Modified Eagle Medium without bicarbonate containing 10% fetal calf serum and 10 mM HEPES, pH 7.2 and were mechanically dissociated by trituration approximately 10 times through a glass Pasteur pipet whose opening had been fire polished and constricted to a diameter such that it took 2 seconds to fill the pipet.

The dissociated ganglia were then plated in culture medium (Dulbecco's Modified Eagle Medium supplemented with 10% fetal calf serum, 4 mM glutamine, 60 mg/L penicillin-G, 25 mM HEPES, pH 7.2) in 100 mm diameter tissue culture dished (40 dissociated ganglia per dish) for three hours. This preplating was done in order to separate the nonneuronal cells, which adhere to the dish, from the nerve cells, which do not adhere. After three hours, the nonadherent nerve cells were collected by centrifugation, resuspended in culture medium, and plated in 50 ul per well onto half area 96 well microtiter tissue culture plates at a density of 1500 nerve cells per well. The microtiter well had been previously exposed to a 1 mg/ml solution of poly-L-ornithine in 10 mM sodium borate, pH 8.4 overnite at 4° C., washed in distilled water and air dried.

Ten ul of a serial dilution of the sample to be assayed for neurotrophic activity was added to each well and the dishes were incubated for 20 hours at 37° C. in a humidified atmosphere containing 7.5% $CO_2$. After 18 hours, 15 ul per well of a 1.5 mg/ml solution of the tetrazolium dye MTT in Dulbecco's high glucose Modified Eagle Medium without bicarbonate containing 10 mM HEPES, pH 7.2, was added and the cultures placed back in the 37° C. incubator for 4 hours. Then, 75 ul of a solution of 6.7 ml of 12M HCl per liter of isopropanol was added and the contents of each well triturated 30 times to break open the cells and suspend the dye. The adsorbance at 570 nm was determined relative to a 690 nm reference for each well using an automatic microtiter plate reader (Dynatech, Chantilly, Va.). The absorbance of wells which had not received any neurotrophic agent (negative controls) was subtracted from the absorbance of sample-containing wells. The resulting absorbance is proportional to the number of living cells in each well, defined as those nerve cells capable of reducing the dye. The number of trophic units on neurotrophic activity was defined as the reciprocal of the dilution that gave 50% of maximal survival of nerve cells. The concentration of trophic activity in trophic units per ml was obtained by dividing the total trophic units by the assay volume (60 ul). Specific activity was determined by dividing the number of trophic units by the amount of protein present in the sample.

C. Purification of SN-CNTF

At the end of each of the following steps, the preparation was either processed immediately or stored at –70° C. for up to one week until used.

Step 1. Crude Extract Preparation

One Hundred grams (wet weight) of rabbit sciatic nerve (about 300 nerves) was thawed and pulverized using a Polytron rotary homogenizer (Kinematica, Switzerland) for 1 minute in 10 volumes (wt/vol) of water containing 10 nM EDTA, 1 nM epsilon aminocaproic acid, 1 mM benzamidine and, 0.1 mM PMSF, and centrifuged at 140,000×g for 30 minutes at 4° C. The supernatant was filtered through glass wool to remove floating lipid.

Step 2. Acid Treatment and Ammonium Sulfate Fractionation

The centrifugation steps referred to below were performed at 17,000×g for 20 minutes and all operations were performed at 4° C., unless otherwise stated. The crude extract was centrifuged. The supernatant was acidified to pH 3.6 with 5N HCl and the resulting precipitate was removed by centrifugation. The supernatant was titrated to pH 6.3 with 1N NaOH and the resulting precipitate was again removed by centrifugation. To the above supernatant was added saturated ammonium sulfate solution to achieve 30% saturation and the precipitate was removed by centrifugation. Further addition of ammonium sulfate to the supernatant to achieve 60% saturation resulted in the precipitation of a protein fraction containing most of the SN CNTF activity.

The precipitate was dissolved in 20 mM sodium phosphate buffer, pH 6.7, containing 1 mM EDTA, 0.1 mM PMSF and 0.1 uM pepstatin, to give a protein concentration of 8-13 mg/ml.

Step 3. Chromatofocussing

The above preparation was dialyzed overnight against a 500 fold larger volume of 10 mM sodium phosphate, pH 6.7 with one change of buffer, and centrifuged at 140.000×g for 30 minutes. The supernatant was passed through 0.22 um pore-diameter nylon filter and loaded in 3 injections of 2 ml each onto a Mono P chromatofocussing FPLC column (bed volume 4 ml) equilibrated in 25 mM bis-Tris-HCl buffer, pH 5.8. The column was washed with the same buffer until the absorbance of 280 nm of the effluent returned to baseline. The sample was then chromatographed with polybuffer, pH 4.0 (1-10 dilution of PB74 from Pharmacia).

Column fractions were collected and analyzed for pH and CNTF activity. FIG. 1 shows the results of chromatography on Mono P. The profile of eluted proteins is plotted as the optical density (O.D.) at 280 nm. Superimposed are plots of the pH and SN-CNTF activity measured in each fraction. The fractions indicated by the bar with peak SN-CNTF activity (around pH 5) were pooled and treated with solid ammonium sulfate to achieve 95% saturation and the pellet was collected by centrifugation, resuspended in saturated ammonium sulfate solution and centrifuged again to remove the polybuffer. The precipitate was dissolved in sufficient 10 nM sodium phosphate buffer, pH 6.7 to give a final protein concentration of 3-5 mg/ml (referred to as the "focussed fraction"). Typically, 1 liter of the original crude extract was processed in 8 separate runs on the Mono P column.

Step. 4. Preparative Sodium Dodecyl

Sulfate (SDS) Gel Electrophoresis

The focussed fractions from multiple runs over the MonoP column were combined and dialyzed against a 100-fold larger volume of 10 mM sodium phosphate buffer, pH 6.7 for 8 hours with one change of buffer, then run on a 15% reducing SDS polyacrylamide slab gel according to the method of Laemmli, 1970. Each resolving gel measured 0.3 cm in thickness, 14 cm in height, and 11.5 cm in width. 5.5 mg of protein was loaded onto each gel. Electrophoresis was performed at 15° C. and 40 mA/gel until the 20 kd prestained molecular weight standard just reached the bottom of the resolving gel.

To reveal the curvature of individual protein bands across the width of the slab gel, the gel was overlayed with a sheet of nitrocellulose (0.45 um pore size in roll form obtained from Millipore Corporation, Bedford, Mass.) prewetted with water, 2 sheets of prewetted and 2 sheets of dry chromatography paper (3 MM Chr obtained from Whatman, Hillsboro, Oreg.), a glass plate and a 500 ml glass bottle for weight. After 30-45 minutes, the outline of the gel was traced onto the nitrocellulose paper using a water-insoluble marker. The paper was washed 3 times with 10 mm Tris-HCl buffer, pH 8.0 containing 0.15M NaCl and 0.3% NP-40 detergent, and then stained for 15-30 minutes with a 1:1000 dilution of Kohinuor Rapidograph Ink (available at stationary supply stores) in the above buffer.

Figure 2:
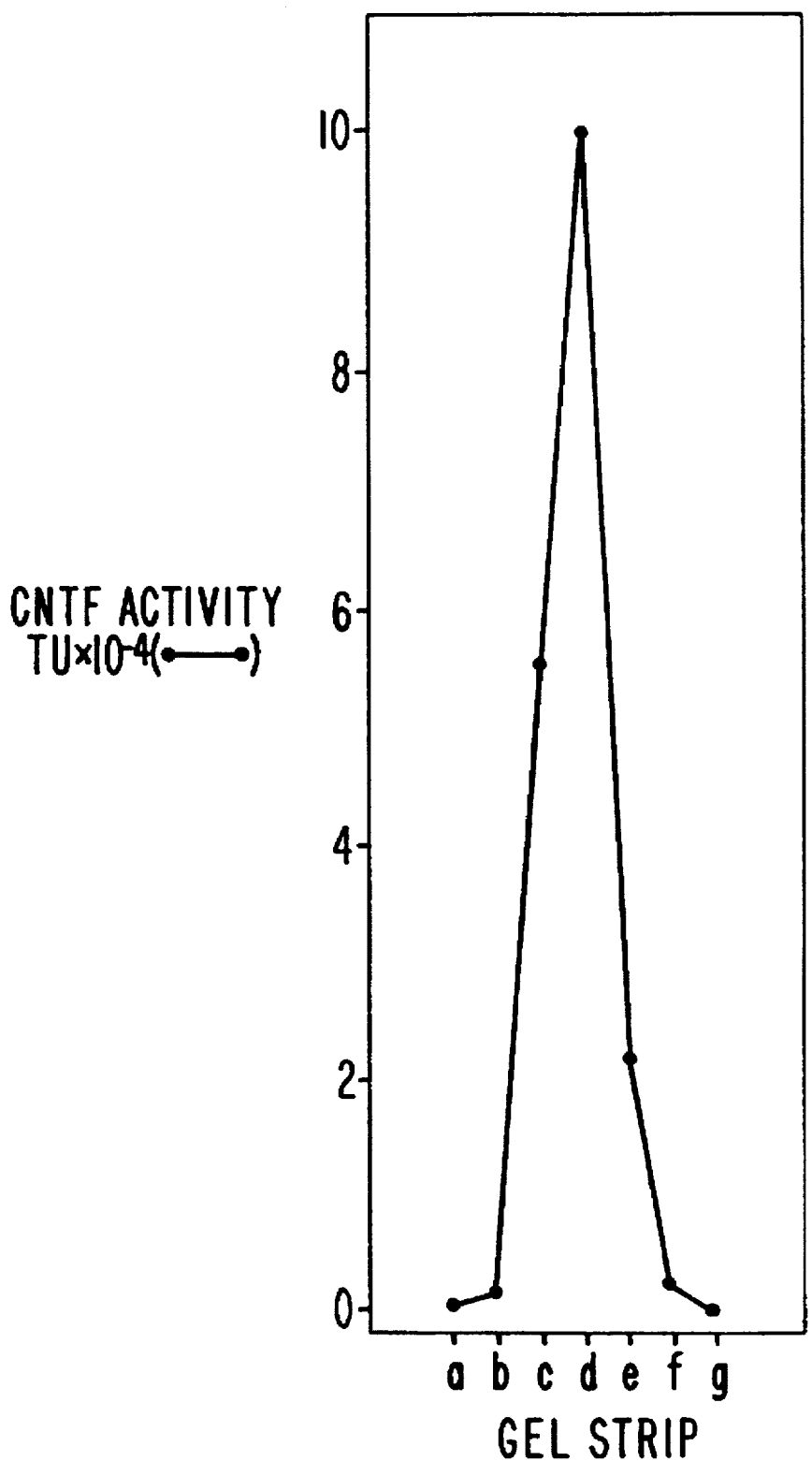
FIG. 2 depicts an exemplary plot of the distribution of neurotrophic activity in the elute from each of the seven strips cut from the SDS-Page gel after electrophoresis.

The original gel was placed onto a glass plate and aligned with its outline on the stained nitrocellulose paper underneath the glass. The region of the gel corresponding to molecular weights between 22-27 kd was located with reference to prestained molecular weight standards (BRL, Bethesda, Md.) run in narrow lanes at both ends of each gel. This region was cut across the width of the gel into seven 2.5 mm parallel strips using the banding curvature revealed by the stained nitrocellulose paper. Each individual gel strip was cut into smaller pieces (2.5×2 mm) and proteins were eluted electrophoretically for 6 hours in a 1:1 dilution of the Laemmli running buffer using an electrophoretic concentrator (ISCO, Lincoln, Neb.). Eluted proteins were collected in a volume of 0.2 ml. FIG. 2 plots the distribution of neurotrophic activity in the elute from each of the 7 strips (labelled a-g in order of decreasing molecular weight). The fraction with the highest activity (strip d) was further purified using reverse-phase HPLC.

Step 5. Reverse Phase—HPLC

Figure 3:
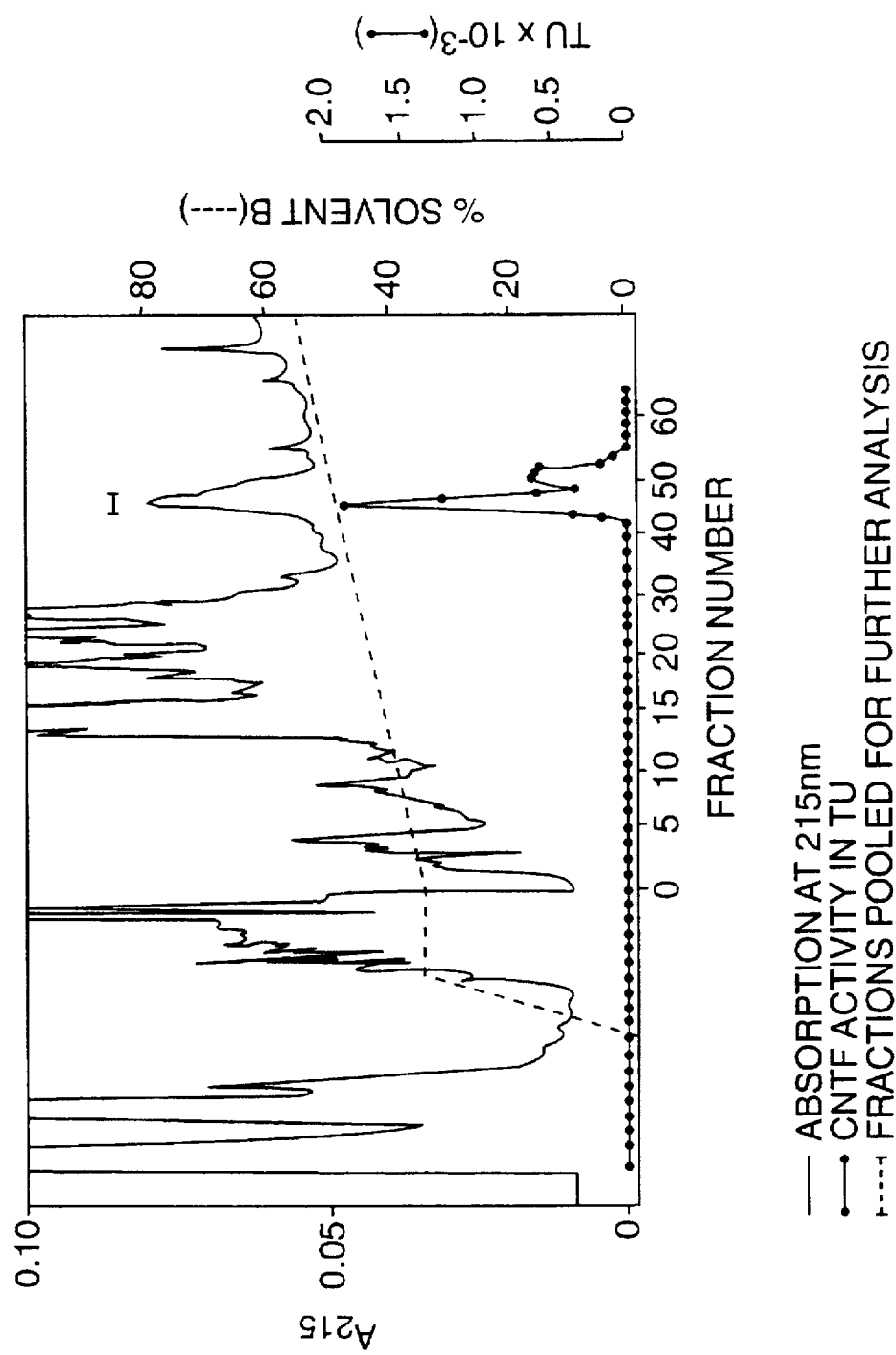
FIG. 3 depicts exemplary results of reverse phase chromatography.
Figure 4:
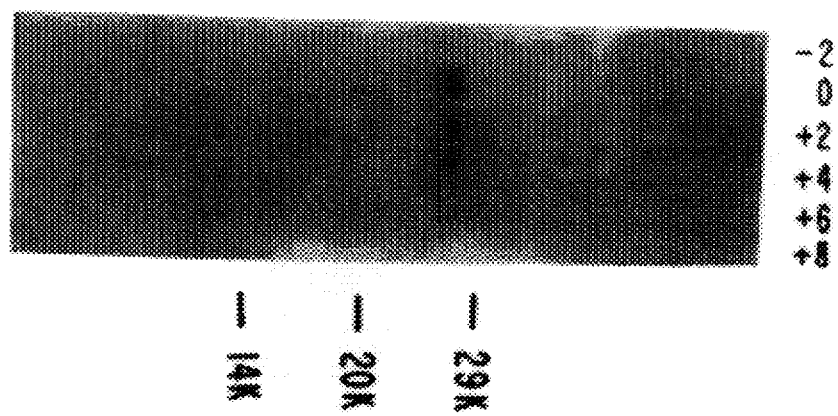
FIG. 4 depicts exemplary results of a silver stained reducing SDS-Page gel run on fractions equivalent to those adjacent to and including the peak of neurotrophic activity shown in FIG. 3.

Dithiothreitol (DTT) and 10% trifluroacetic acid (TFA) were added to the gel eluate to achieve final concentrations of 2% and 0.3%, respectively. The sample was filtered through a 0.22 um nylon filter, loaded onto a C8 reverse phase HPLC column and eluted with an $H_2O/0.1\%$ TFA:acetonitrile/0.1% TFA gradient. Fractions were collected into siliconzied tubes containing 5 ul of 0.4% Tween 20 detergent. Aliquots for each fraction were assayed for neurotrophic activity. FIG. 3 shows the results of reverse phase chromatography. Protein concentration is indicated by absorbance at 215 nm and the distribution of neurotrophic activity is superimposed. Fractions with the peak SN-CNTF activity (fractions 37-40, FIG. 3) were pooled for sequencing as described in Example 2. In a separate preparation, fractions adjacent to and including the peak CNTF activity, equivalent to fractions 36-44 in FIG. 3, were also analyzed on silver-stained reducing SDS-PAGE (FIG. 4).

Two additional chromatographic steps have also been performed. These steps confirmed the purity of the CNTF prepared above.

The two additional chromatographic steps both use the principle of hydrophobic interaction chromatography (HIC). The first HIC step is a conventional column chromatographic procedure inserted after step 2: pH and ammonium sulfate fractionation. The dissolved material after ammonium sulfate precipitation was further diluted with 10 mM sodium phosphate buffer, pH 6.7 (Buffer B) until the ionic strength (measured with a conductance meter) was equal to that of Buffer B containing 0.3M ammonium sulfate and 5% isopropanol (Buffer A). Isopropanol was then added to the diluted sample to a final concentration of 5% and the mixture applied to a column of phenyl-Sepharose CL4B (Pharmacia, Inc., Piscataway, N.J.) equilibrated with Buffer A. No more than 3 mg of sample protein was applied per ml of column bed-volume. Typically, 1 liter of crude sciatic nerve extract yielded 50 ml. of the redissolved ammonium sulfate pellet, which was then diluted to 70-100 ml as above and applied to a 110 ml phenyl Sepharose column. The column was eluted stepwise starting with 3 bed-volumes of Buffer A, followed by 3 bed-volumes of Buffer B, followed by 2 bed-volumes of Buffer B containing 50% ethylene glycol (Buffer C), then washed with 5 bed-volumes of water. Eighteen ml fractions of the eluted material were collected.

Figure 7:
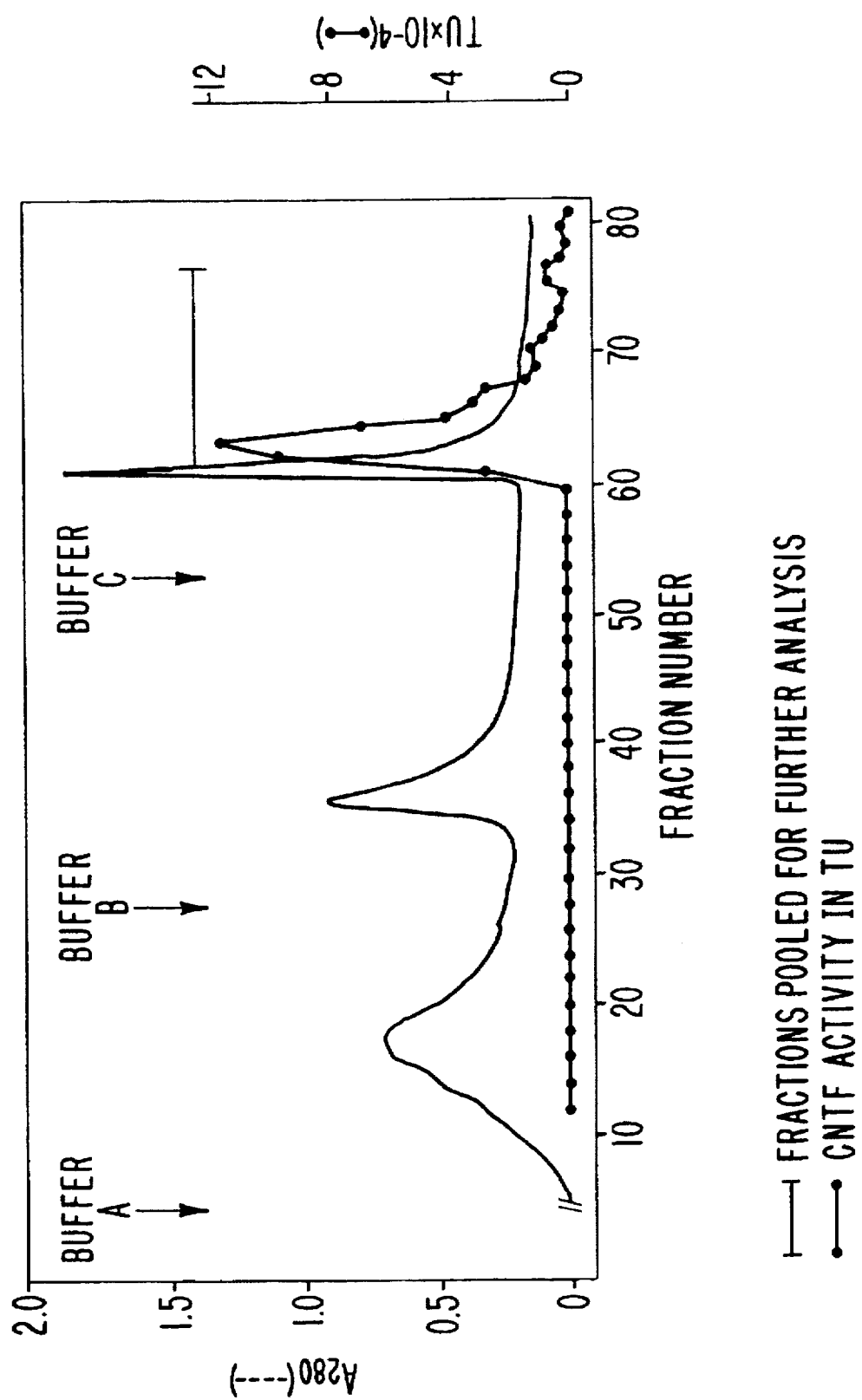
FIG. 7 depicts exemplary results of chromatography of the ammonium sulfate fraction on a phenyl Sepharose HIC column.

FIG. 7 shows the results of one such chromatography run. The profile of eluted proteins was continuously monitored by O.D. 280 (solid line). Superimposed on the O.D. tracing is the profile of eluted SN-CNTF bioactivity in each fraction (line connecting x's), as measured in the ciliary ganglion survival assay described in the original patent application. SN-CNTF bioactivity emerged from the column during elution with Buffer C. The column fractions containing the bulk of the bioactivity (indicated by the bar in FIG. 7) were pooled and concentrated by pressure dialysis using an Amicon YM-10 membrane (Amicon Division, W.R. Grace & Co., Danvers, Mass.) to approximately 1/10 of the original volume, which typically resulted in a final protein concentration of 2.5–3.0 mg/ml. The concentrate was dialyzed for a total of 6 hr against 3 changes of 55-fold larger volume of B. The dialyzed material was passed through a 0.2 µm pore diameter Acrodisc filter (Gelman Sciences, Inc., Ann Arbor, Mich.) and loaded in multiple injections of 2 ml each onto a Mono-P chromatofussing column as described in the original patent application.

Without this HIC column step, 1 liter of crude sciatic nerve extract required 8 separate runs on the Mono-P chromatofocussing column, as described in the initial patent application, because of the limited protein loading capacity of the column. With the addition of the HIC column step, 1 liter of crude extract could be processed in a single chromatofocussing run.

The second HIC step was inserted after the original step 3: chromatofocussed on Mono-P. To every 1 ml of the chromatofocussed material (at 3–5 mg/ml of protein) was added 2 ml of 50 mM phosphate buffer, pH 6.7, containing 1.5M ammonium sulfate (Buffer D). The mixture was then passed through a 0.2 µm pore diameter Acrodisc filter and loaded in multiple injections of 2 ml each onto a Alkyl-Superose HR10/10 FPLC column (Pharmacia) equilibrated with Buffer D. The column was washed with Buffer D until the absorbance of the affluent a O.D. 280 returned to baseline. The column was then eluted with a 60 ml linear gradient running from Buffer D into Buffer E (50 mM phosphate buffer, pH 6.7) and 1 ml fractions were collected.

Figure 8:
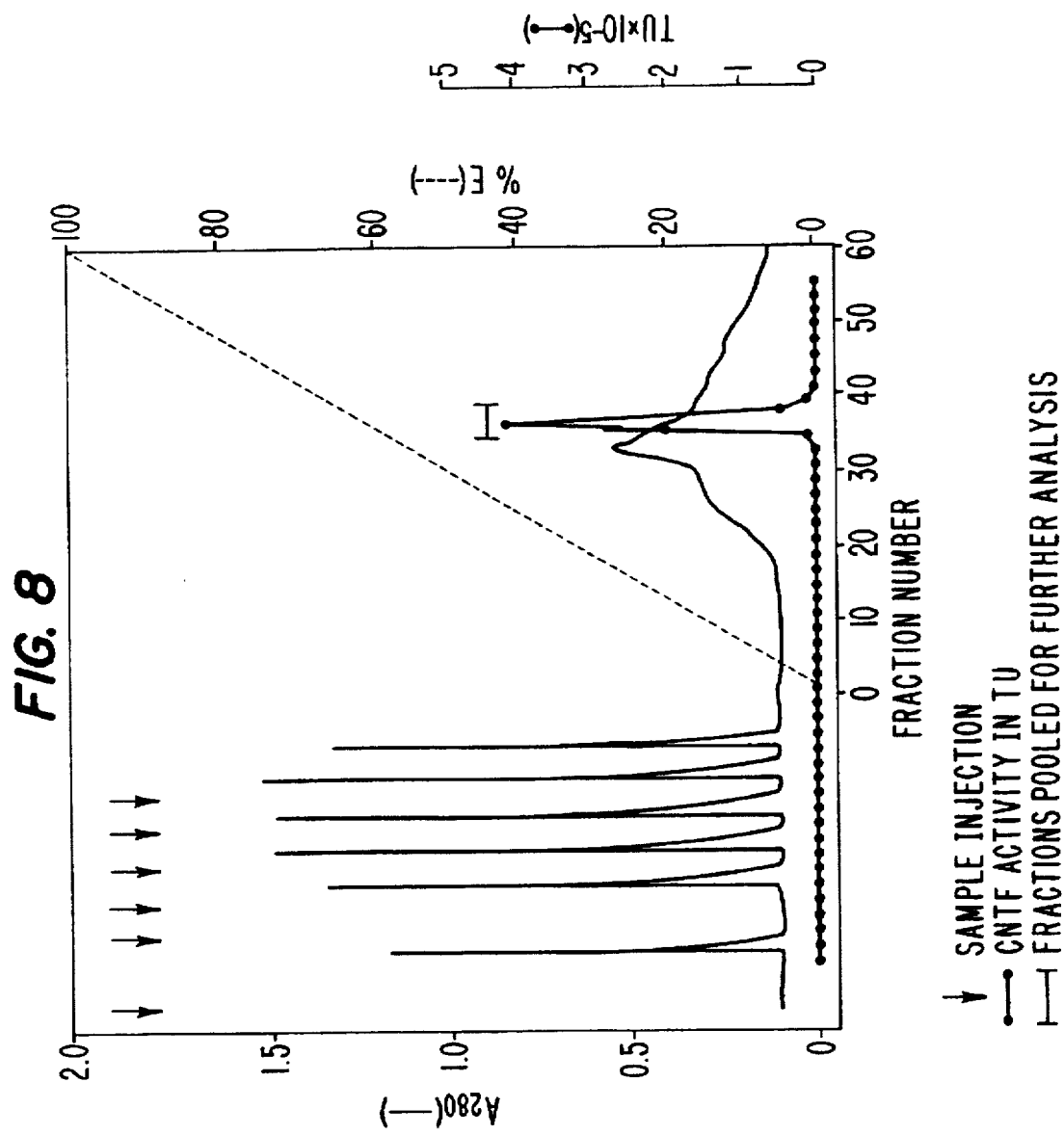
FIG. 8 depicts exemplary results of chromatography of the Mono-P chromatofocussed fraction on a alkyl-Superose FPLC-HIC column.

FIG. 8 illustrates the results of one such FPLC-HIC column run. The continuous line represents the profile of eluted protein measured by O.D. 280. Superimposed is a plot of the SN-CNTF bioactivity in each gradient fraction. The fractions containing bioactivity (indicated by the bar in FIG. 8) were pooled and concentrated in a Centricon-10 concentrator (Amicon) to 0.5 ml. The sample was diluted by adding 2 ml of Buffer B to the upper reservoir and reconcentration by centrifugation to a final volume of 0.5 ml. Dilution and reconcentration was repeated 2 additional times and the final concentrated sample was run on a reducing SDS-15% polyacrylamide preparative slab gel as described above, except that prior dialysis was not necessary.

Figure 9A:
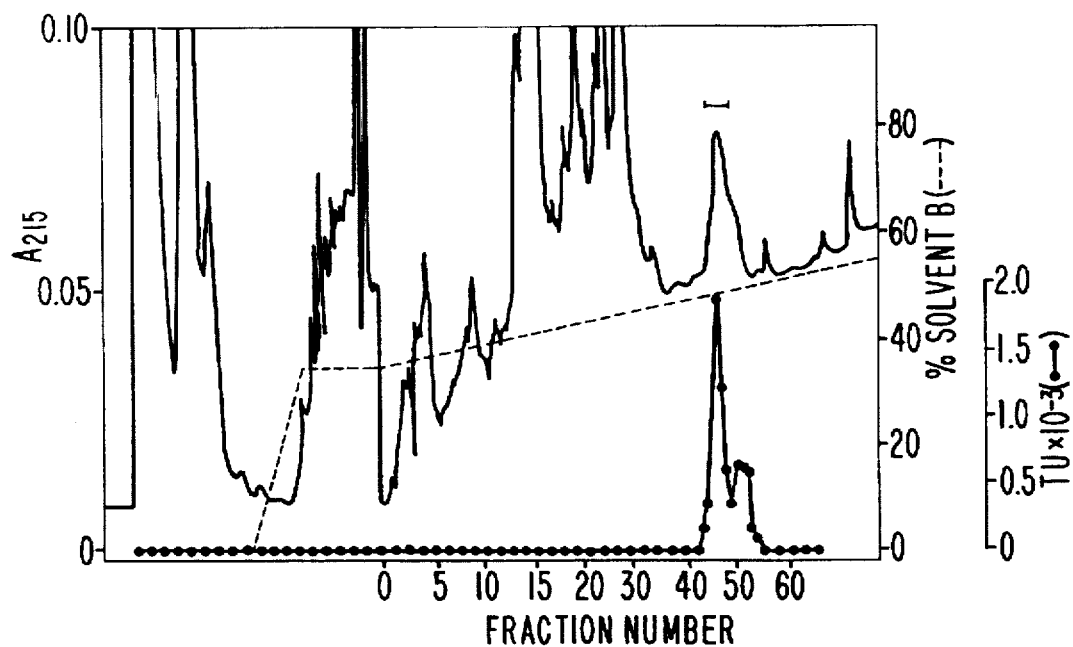
FIG. 9 depicts exemplary results of chromatography of the preparative SDS-PAGE fraction of a C8 reverse-phase HPLC column. Panel (A) illustrates the results of the original purification procedure. Panel (B) illustrates the results of the current purification procedure after addition of the two HPLC chromatography steps.
Figure 9B:
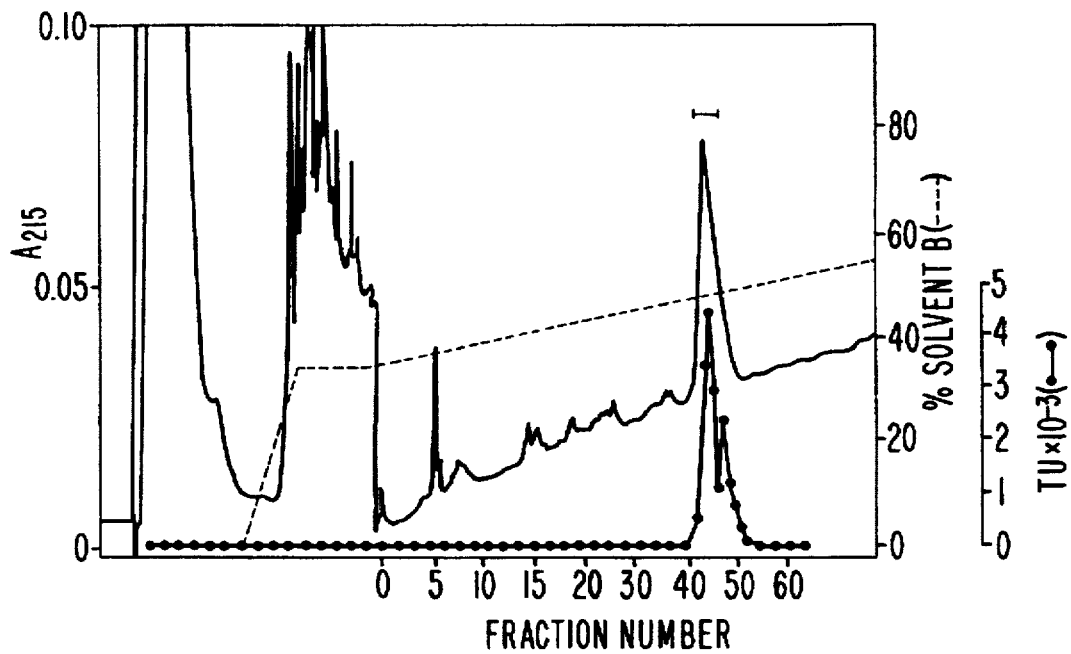

FIG. 9 compares the final purification step on reverse phase HPLC in the initial purification procedure (upper panel) and in the purification procedure after addition of the two HIC steps (lower panel). Each panel shows the profile of eluted proteins (solid line is O.D. 280 and the superimposed SN-CNTF bioactivity (line connecting x's). It is apparent from the Figure that there is much less contaminating protein present in the sample put onto reverse phase HPLC in the new purification procedure. It is important to note that the specific activity of CNTF produced by the new procedure is identical within experimental error with the specific activity of CNTF produced by the previous procedure (Table 1), indicating that the CNTF prepared by the original procedure described above was purified to homogeneity. The advantage of the new purification procedure is that 8 liters of starting material can now be processed as conveniently as 1 liter using the original procedure.

EXAMPLE 2

Sequencing of the Purified Neurotrophic Factor

Figure 5:
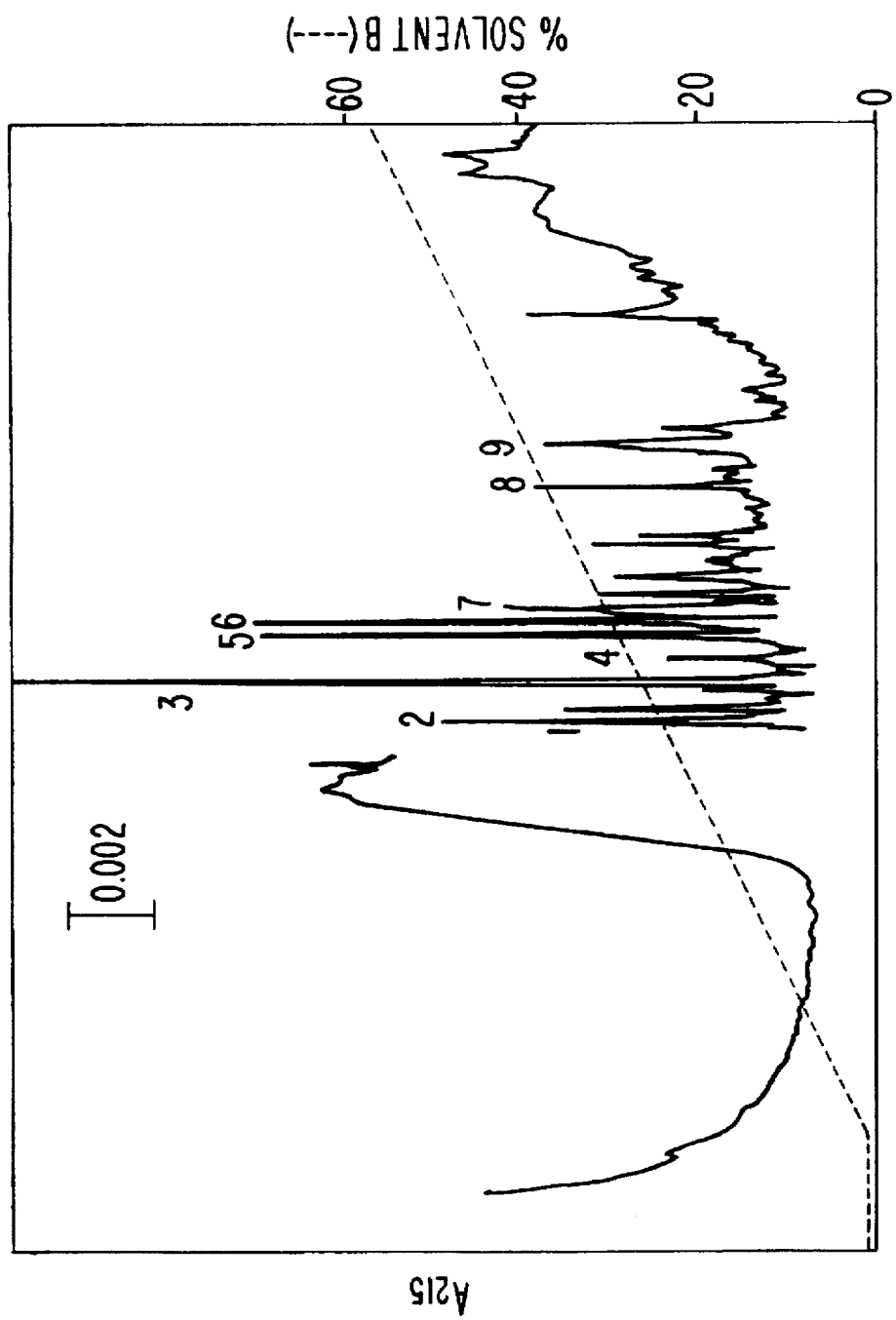
FIG. 5 depicts a profile of eluted peptides after digestion with endoprotease Asp-N.
Figure 6:
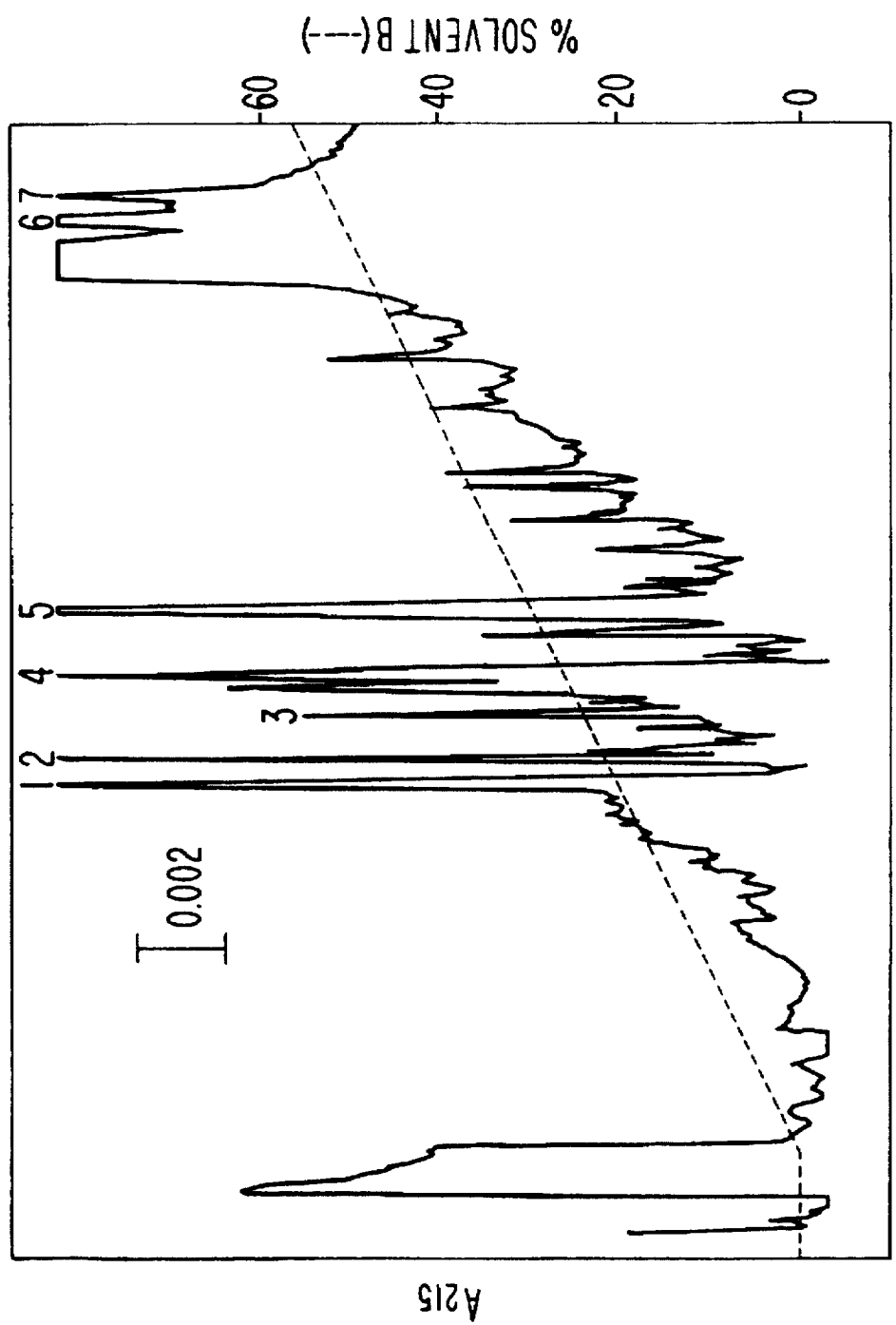
FIG. 6 depicts a profile of eluted peptides after digestion with endoprotease Lys-C.

Fractions with the peak SN-CNTF activity (#37–40, FIG. 3) were pooled and concentrated to 50 ul on a vacuum centrifuge. The concentrated sample contained 0.14% Tween 20. It was diluted with 1% ammonium bicarbonate to a final volume of 350 ul an treated with endoprotease Asp-N or endoprotease Lys-C overnight at 37° C. The mixture was concentrated to approximately 50–100 ul on an vacuum evaporator centrifuge and loaded via a 1 ml sample loop onto a narrow bore Aguapore RP-300 C8 reverse phase HPLC column (Brownlee Labs), 2.1×220 mm, eluted with an $H_2O/0.1\%$ TFA:acetonitrile/0.1% TFA gradient. Peptide containing fractions were collected manually into Eppendorf tubes based on the absorption at 215 nm. FIG. 5 shows the profile of eluted peptides after digestion with endoprotease Asp-N as determined by absorbance at 215 nm. FIG. 6 shows the profile of eluted peptides after digestion with endoprotease Lys-C followed by reduction and carboxmethylation. The amino acid sequence of the prominent peptides was determined using an Applied Biosystems gas phase protein sequencer.

Additional amino acid sequence has been obtained with the cleavage enzymes chymotrypsin and endoprotease Glu-C (Boehringer Mannheim Biochemicals, Indianapolis, Ind.). This additional protein sequence has allowed some of the amino acid sequences reported above to be pieced together into larger peptides from overlapping stretches of amino acids. The new amino acid sequences and those joined together with previous sequences are given below:

H—S—A—L—T—P—H—R—R—E

L—A—R—K—I—R—S—D—L—T—E—S—Y—V—K—H—
Q—G—L—N—K—N—I—N—L—D—S—V—D—G—
V—P—M—A—

D—Q—Q—V—H—F—T—P—A—E—G

D—G—L—F—E—K—K—L—W—G—
L—K—V—L—Q—E—L—S—H—W—T—V

D—L—R—V—I

EXAMPLE 3

Preparation of Antibodies to the Neurotrophic Factor

Antibodies that react with purified rabbit SN-CNTF will be useful for screening expression libraries in order to obtain the gene which encodes rabbit SN-CNTF. In addition, antibodies that neutralize its biological activity will be used in intact animals in order to determine the biological role of this neurotrophic factor.

In order to prepare such antibodies, synthetic peptides will be synthesized which correspond to regions of the sequence of SN-CNTF using an Applied Biosystems automated protein synthesizer. Such synthetic peptides will be covalently linked to the carrier protein keyhold limpet hemocyanin. The conjugated peptide will be injected into guinea pigs in complete Freund's adjuvant, with booster shots applied at 3 and 6 weeks in incomplete adjuvant. Serum samples will be taken from each guinea pig and used in a Western blot against purified SN-CNTF in order to determine if antibody in the serum reacts with the purified protein. Sera positive in the Western assay will be further tested for ability to neutralize the neurotrophic activity in the bioassay used for purification. Sera positive in either the Western or neutralization assay will be further purified as follows: (1) the sera will be absorbed with the carrier protein keyhole limpet hemocyanin in order to remove antibodies directed against that protein, then the sera will be retested in the above assays; (2) the IgG antibody fraction will be purified from the serum by standard procedures and retested in the above assays. Both these steps will provide a polyclonal antibody that is pure enough to be used to screen expression libraries in order to clone the messenger RNA and gene for SN-CNTF.

Antibodies were generated in rabbits to a synthetic peptide "A" corresponding to a portion of the amino acid sequence of rabbit SN-CNTF given in Example 2 (E-S-Y-V-K-HQ-G-L-N-K-N). Methods are given in detail below in this Example. Affinity-purified antibodies against synthetic peptide A (anti-peptide-A antibodies) were prepared by passing immunized rabbit antiserum over an affinity column containing covalently-linked synthetic peptide A and then eluting bound antibodies. The unfractionated immune antiserum gave a titer of ca. $10^5$ in an ELIZA assay using peptide A coated wells: it was used at a 1:50 final dilution for Western blot analysis. The affinity-purified anti-peptide-A antibody, prepared as described below, was used in Western blot analysis at a final concentration of 80 µg/ml.

Both the anti-peptide-A antiserum and affinity-purified antibodies were demonstrated to interact with purified rabbit SN-CNTF by Western blot analysis of reducing SDS-polyacrylamide-gel electrophoresis (SDS-PAGE) of purified CNTF. Pre-immune serum from the same rabbit did not interact with SN-CNTF under these conditions. Aliquots of the peak fraction of CNTF from the final reverse-phase HPLC purification step (fraction #46, FIG. 9, panel B) were run in two separate lanes on reducing SDS-PAGE. Adjacent to each lane of purified CNTF was a lane containing molecular weight marker proteins. The gel was cut into two panels each of which contained one lane of purified CNTF and an adjacent lane of marker proteins. One of the pieces was silver-stained to localize proteins (Bio-Rad Laboratories, Richmond, Calif.) and the other was examined by Western blot analysis (Towbin et al., 1979, *Proc. Natl. Acad. Sci., U.S.A.* 76:4350) for proteins that reacted with the affinity-purified anti-peptide-A antibodies.

Figure 10A:
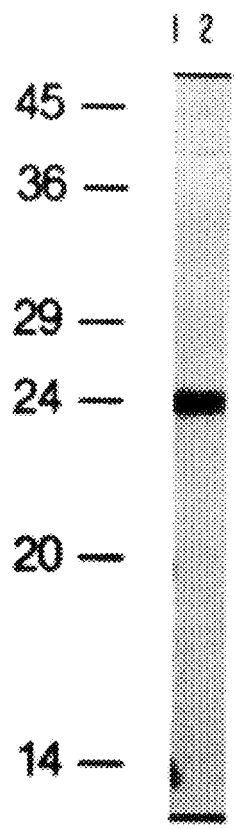
FIG. 10 depicts exemplary results of SDS-PAGE and Western blot analysis of the reverse-phase purified SN-CNTF. Lane 1 in each of the two panels contains molecular weight standard proteins (SIGMA SDS-7). Lane 2 contains purified SN-CNTF. Panel (A) illustrates the results of silver-staining. Panel (B) illustrates the results of Western blot analysis with affinity-purified anti-peptide-A antibody.
Figure 10B:

The left-hand panel of lanes in FIG. 10 demonstrates that the peak fraction of reverse-phase purified CNTF contains two closely-spaced protein bands that run at approximately 25,000 daltons and are separated from each other by approximately 500 daltons on reducing SDS-PAGE. When silver-stained gels are overloaded with purified CNTF, it is often not possible to resolve the two bands as in FIG. 4.

The right hand panel of lanes in FIG. 10 demonstrates that both of these bands are recognized and stained by affinity-purified anti-peptide-A antibodies. This recognition is specific since the unrelated marker proteins in the left-most lane of the right-hand pair are not recognized by the anti-peptide-A antibodies, although they are present in high concentration as demonstrated in the left-hand silver-stained lanes (FIG. 10). The pre-immune serum from this same rabbit also does not recognize the two bands of purified CNTF. These results indicate that there are at least two different forms of CNTF which differ by ca. 500 daltons in molecular weight on reducing SDS-PAGE.

To prepare anti-peptide-A antibodies, synthetic peptide A was conjugated to Keyhole Limpet Hemocyanin (KLH) to enhance its antigenicity. For conjugation, 1 mg of peptide A and 1 mg of KLH (Calbiochem, La Jolla, Calif.) in 50% glycerol were dissolved in 0.5 ml of PBS (20 mM sodium phosphate buffer, pH 7.4, containing 0.15M NaCl). 10% glutaraldehyde was added dropwise with mixing to a final concentration of 1%, and the reaction was allowed to stand at room temperature overnight with mixing, then diluted to 5 ml with PBS. The conjugation mixture was emulsified 1:2 with complete Freund's adjuvant and injected subcutaneously into multiple dorsal sites in two New Zealand white rabbits at ca. 100 µg peptide A per rabbit. Three weeks later, each rabbit received a booster dose of 50 µg of conjugated peptide A in incomplete Freund's adjuvant. Thereafter, similar booster injections were administered at 2-week intervals until the antiserum gave a titer of at least 100,000 in an ELIZA assay (Tainer et al., 1984, *Nature* 312:127) using peptide A-coated wells. Sera were prepared from blood collected from the ear vein 5 weeks after the initial injection and biweekly thereafter. Sera were stored at −70° C.

To prepare a peptide affinity column, peptide A was covalently attached to a chromatography column matrix as follows: To 8 mg of peptide A dissolved in 0.4 ml of PBS containing 4M guanidine hydrochloride was added 4.5 ml of 0.1M NaHCO$_3$, pH 8.0, and 0.5M NaCl. One gram of freeze-dried activated CH Sepharose 4B (Pharmacia) was washed and swelled in 200 ml of 1 mM HCl and immediately transferred to the solution of peptide A. The mixture was rocked overnight at 4° C. The gel was then sedimented in a clinical centrifuge and the supernatant saved for determining the amount of peptide A that became coupled to the matrix. Fifteen ml of 0.1M TRIS buffer, pH 8.0, was added to the gel pellet and incubated at room temperature for 2 hr to block unreacted coupling groups on the gel matrix. The gel was then packed into a column (3 ml bed) and washed three times with the following buffer sequence: (1) 10 bed volumes of 0.1M acetate buffer, pH 4.0, containing 0.5M NaCl; (2) 0.1M TRIS buffer, pH 8.0, containing 0.5M NaCl. Finally, the column was equilibrated with PBS containing 0.02% sodium azide. The difference in the concentration of free amino groups was determined in the original peptide A solution and in the supernatant after conjugation, using fluorescamine (Chen et al., 1978, *Arch. Biochem. Biophys*, 189:241, Nowicki, 1979, *Anal. Letters* 12:1019). This analysis showed that 92–95% of the peptide was lost from solution and had become conjugated to the Sepharose gel matrix.

Prior to affinity purification of the anti-peptide A antibody, 8 ml of immunized rabbit serum was dialyzed overnight against 2 liters of PBS. The peptide A-Sepharose column was washed sequentially with 10 bed-volumes of each of the following: 0.1M glycine-HCl, pH 2.5; PBS; 0.1M triethylamine, pH 11.5; then PBS. The dialyzed serum was passed through the column three times to insure complete binding of anti-peptide-A antibodies. The column was washed with 20 bed-volumes of PBS, then eluted sequentially with 4 bed-volumes each of the following: 0.1M glycine-HCl, pH 2.5; PBS; 0.1M triethylamine, pH 11.5; then PBS. One ml fractions were collected. The eluates from the glycine and triethylamine washes were neutralized immediately with 1M TRIS, pH 9 and 7, respectively, and aliquots assayed for anti-peptide A antibody with an ELIZA assay using peptide A-coated wells. The highest titer fractions (typically within 3 bed-volumes of the start of glycine and triethylamine elution) were pooled and dialyzed against PBS. After removing particulate matter by brief centrifugation, the affinity-purified anti-peptide A antibody supernatant was stored at −70° C.

EXAMPLE 4

Cloning the Gene for SN-CNTF

The ultimate goal of the work to be described is to clone and express the human SN-CNTF gene in order to prepare material suitable for use in human pharmaceutical preparations. Since the peptide sequences obtained are for rabbit SN-CNTF and the rabbit and human sequences may not be identical, it is prudent to first obtain clones of the rabbit gene via hybridization with synthetic oligonucleotides based on the protein sequence and to employ the rabbit clones as hybridization probes in screens for the human gene.

Both the genomic and messenger RNA (mRNA) sequences encoding rabbit and human SN-CNTF will be obtained. The mRNA sequence will be useful for expressing the protein, whereas the genomic sequence will be essential for understanding the structure and regulation of the gene for SN-CNTF. In order to obtain these sequences, both rabbit and human genomic libraries and rabbit and human cDNA libraries made from mRNA isolated from sciatic nerves will be screened. In the process of obtaining the gene corresponding to the sequence of rabbit or human SN-CNTF, it is also possible to screen for structurally closely related genes that may represent additional members of this family of neurotrophic factors.

A. SN-CNTF Gene

To isolate the rabbit genomic sequences encoding SN-CNTF, a rabbit genomic library (Clontech) will be plated on the *E. coli* nm538 bacterial strain and approximately 1,000,000 recombinant clones will be screened. Regions of the protein sequence of rabbit SN-CNTF that can be represented by the fewest codons will be reverse-translated and corresponding degenerate oligonucleotide probes will be synthesized. The rabbit oligonucleotides will be labeled by kinasing according to the standard protocol of Maniatis et al. (1982, Molecular Cloning, A Laboratory Manual, Cold Spring Harbor Laboratory). The DNA kinase is obtained from US Biochemical Corp. and the gamma labeled ATF is obtained from ICN. Oligonucleotides will be labeled to a specific activity of at least 1,000,000 cpm per picomole.

Upon plating of the genomic library, approximately 1 million plaques will be transferred onto duplicate nitrocellulose filters. The filters will then be processed according to the methods of Maniatis et al. (1982, ibid.) and hybridized overnight with radioactively-labeled oligonucleotide probe. The hybridization cocktail will include 6× SSCP, 2× Denhardt's, 0.05% sodium pyroophosphate, 1 mM EDTA, 0.1% SDS, 100 ug yeast rRNA (Sigma), pH 8.0. The temperature of hybridization will be several degrees below the calculated Tm of the oligonucleotide. Clones that hybridize with several probes based on different regions of the protein sequence will be plaque purified and the regions of hybridization will be sequenced by dideoxy termination method (Sanger et al., 1977, Proc. Natl. Acad. Sci. 74:5463) using Sequenase (US Biochemicals Corp.) in order to identify those clones that encode the SN-CNTF protein sequence.

B. SN-CNTF mRNA Sequences

Total cellular RNA will be obtained from rabbit and human sciatic nerves. The tissue will be homogenized in a guanidinium thiocyanate/beta-mercaptoethanol solution and the RNA will be purified by sedimentation through cesium chloride gradients (Glison et. al., 1974, Biochemistry 13:2633). Polyadenylated RNA will be selected by chromatography on oligo(dT)cellulose (Avid and Leder, 1972, Proc. Natl. Acad. Sci. 69:408). Quantitative RNA blot hybridization analysis will be performed with "antisense" oligonucleotide probes to estimate the prevalence of SN-CNTF sequences in each RNA preparation and to thereby estimate the number of independent clones one would need to screen to have at least a 99% probability of obtaining CNTF clones. Sufficient doublestranded complimentary DNA will be synthesized as described by Gubler and Hoffman, 1983, Gene 25:263, and inserted into the lambda gem2 vector (Promega Biotech) according to Palazzolo and Meyerowitz, 1987, Gene 52:197.

Rabbit SN-CNTF encoding clones will be identified by hybridization of recombinant phage plaques as described above. The identities of the clones will be verified by determination of nucleotide sequences in order to determine correspondence with the entire known protein sequence. Screens of the human sciatic nerve cDNA library will be conducted with randomly primed rabbit SN-CNTF cDNA probes (Feinberg and Vogelstein, 1983, Anal. Biochem. 132:6), which is a more reliable procedure for detecting cross-species hybridization than the use of the smaller oligonucleotides used to screen the rabbit cDNA libraries.

The Polymerase Chain Reaction (PCR) (Saiki et al., 1988, *Science* 239:487) was used to amplify DNA fragments corresponding to rabbit CNTF amino acid sequences. Such DNA fragments were amplified from human and rabbit genomic DNA and rabbit sciatic nerve and sympathetic ganglion cDNA. The amplified DNA fragments were subcloned and sequenced using standard techniques (Maniatis et all., 1982, Molecular Cloning: A laboratory manual, Cold Spring Harbor, N.Y.).

The DNA fragments obtained by PCR were also used as probes to screen a rabbit sciatic nerve cDNA library and a human genomic DNA library. A positive rabbit cDNA clone and positive human genomic clones were purified and partially sequenced. The sequence of the open reading frame corresponding to the coding (mRNA equivalent) sequence for rabbit or human CNTF confirmed the sequence of the DNA fragments of the coding region obtained using PCR. The resulting coding sequences for rabbit and human CNTF are given in FIGS. 11 and 12, respectively.

Portions of the amino acid sequence obtained from rabbit SN-CNTF were reverse translated into the degenerate oligonucleotide #'s 1, 13, 7, and 12 and their complements #'s 3, 14, 8, and 17. The amino acid sequence (on top) and the location and numbering of the corresponding sense and anti-sense degenerate oligonucleotides (underneath) is given below:

```
         Y—V—K—H—Q—G—L—N—K—N—I—N—L—D—S—V—D—G—V—P—M—A (5')  **1**         13*         *7***(3')

(3')  **3**         14*         *8***(5')

K—L—W—G—L—K—V—L—Q—E—L—S
```

(5')  \*\*\*\*12\*\*\*\*\*(3')

(3')  \*\*\*\*17\*\*\*\*\*(5')

The nucleotide sequence of the sense version of each of the degenerate oligonucleotides is given below (where N corresponds to any nucleotide):

1 5'-TA(T/C) GTN AA (A/G) CA(T/C) CA(A/G) GG -3'
13 5'-AA(T/C) AA(A/G) AA(T/C) AT(A/T/C) AA (T/C) (C/T)T -3'
7 4'-GA(T/C) GGN GTN CCN ATG GC -3'
12A 5'-AA(A/G) TT(A/G) TGG GGN TT(A/G) AA -3'
12B 5'-AA(A/G) TT(A/G) TGG GGN CTN AA -3'
12C 5'-AA(A/G) CTN TGG GGN TT(A/G) AA -3'
12D 5'-AA(A/G) CTN TGG GGN CTN AA -3'

Separate Polymerase Chain Reactions were performed using either human or rabbit genomic DNA as template and oligonucleotide #'s 1 and 8 or #'s 1 and 17 as primers, in order to amplify the corresponding regions of the human and rabbit CNTF genes. Southern blots of the reaction products (probed with radiolabeled oligonucleotide #13) revealed the existence of labeled bands ca. 66 base pairs (#'s 1 and 8) and ca. 366 base pairs (#'s 1 and 17) in size.

The same PCR reactions described above were run using cDNA prepared either from rabbit sciatic nerve or rabbit sympathetic ganglion mRNA. RNA was prepared from rabbit sciatic nerves or sympathetic ganglia and passed over an oligo-dT column to select for messenger RNA (mRNA), as described above. Complementary DNA (cDNA) was prepared with reverse transcriptase using the mRNA as template and oligo-dT as primer. When PCR was performed using either cDNA as template and either oligonucleotide #'s 1 and 8 or #'s 1 and 17 as primers, fragments were amplified which had the same sequence as those amplified from the rabbit genomic DNA (FIG. 11). This indicates that there are no intervening sequences (introns) in the protein coding region of the CNTF gene between oligonucleotides #'s 1 and 17.

An additional strategy was used to obtain more of the coding (messenger RNA equivalent) sequence for rabbit CNTF: Double-stranded cDNA was prepared using rabbit sciatic nerve mRNA as template and an oligo-dt/Not I linker adapter as primer. Subsequently, an EcoRI/XmnI-linker adapter (5'-AATTCGAACCCCTTCG-3') was added to the 5'-end of the double-stranded cDNA by blunt-end ligation (Maniatis et al., ibid.). The Polymerase Chain Reaction was performed using this cDNA as a template and oligonucleotides #8 and EcoRI/XmnI-linker-adapter as primers. A Southern blot of the reaction products (probed with radiolabeled oligonucleotide #13) revealed the existence of a labeled band approximately 200 base pairs in size.

To obtain cDNA clones for rabbit CNTF, a cDNA library was prepared from rabbit sciatic nerve poly(A)+mRNA by the methods described above, except for the use of a lambda gt10 vector (Stratigene) in place of lambda gem2. Approximately 4×10⁶ plaques of this library were screened using a probe prepared by randomly labeling an M13 subclone of a PCR fragment obtained from rabbit sympathic ganglion cDNA as template and oligos #8 and Eco RI/Xmn I liker adapter as primers (see above). The single primary positive was plaque purified through a tertiary screen. Upon digestion with Eco RI, the DNA from this clone yielded three fragments in addition to the lambda arms: ca. 2.0, 1.5, and 0.6 kb in length. By Southern blot analysis the 1.5 kb fragment was shown to hybridize to other CNTF-specific oligonucleotides and PCR fragments referred to above. The DNA sequence of this 1.5 kb cDNA fragment established that it contained the entire coding sequence for rabbit CNTF (FIG. 11).

To obtain genomic DNA clones for human CNTF, approximately 3×10⁶ plaques of a human genomic DNA library in vector lambda EMBL3 were screened using a probe prepared by randomly labeling an M13 subclone of a PCR fragment obtained from human genomic DNA as template and oligos #1 and #17 as primers (see above). Six of the primary positives were plaque purified by subsequent screening and found to hybridize to additional CNTF-specific oligonucleotides and PCR fragments. A 0.6 kb Bam HI restriction fragment from one of the clones hybridizing to oligo #13 was subcloned into Bam HI-cut M13mp19 and sequenced.

The DNA sequences of the fragments obtained by PCT from rabbit material from the rabbit cDNA clone were combined based on regions of overlapping sequence to give the cloning (mRNA equivalent) sequence for rabbit SN-CNTF presented in FIG. 11. The DNA sequences of the fragments obtained by PCR from human genomic DNA and from human genomic clones were combined based on regions of overlapping sequence to give the coding sequence for human SN-CNTF presented in FIG. 12. The rabbit and human nucleic acid sequences for CNTF are ca. 89% identical (FIG. 12), indicating that the rabbit and human sequences are from homologous gene encoding CNTF. As shown in FIG. 11, parts of the nucleic acid sequence for rabbit CNTF are confirmed by the amino acid sequences obtained from purified SN-CNTF and reported in earlier examples.

The Polymerase Chain Reaction was performed using the templates and primers described above. The program for the reactions was as follows: denaturation cycle, 1 min. at 95° C.; annealing cycle, 1.5 min. at 40° C.; and extension cycle, 4 min. at 72° C. The reaction was performed for 30 cycles. The reaction products were electrophoresed through 2% agarose gels and transferred onto Zeta-Bind membranes (BioRad, Richmond, Calif.) for Southern blotting. In order to identify the amplified portions of the CNTF coding sequence, the Southern blots were probed with a radiolabeled oligonucleotide #13, known from the CNTF protein sequence to lie between the oligonucleotides used to prime the reaction. The labeled bands obtained after Southern blotting were cut from the original gels and prepared for cloning by repairing the ends with Klenow fragment of the DNA polymerase (New England Biolabs, Beverly, Mass.) in the presence of all four dNTPs and kinasing the DNA by with T4 polynucleotide kinase (U.S. Biochemical Corp., Cleveland, Ohio) and ATP. The appropriate DNA pieces were then subcloned into M13mp10 SmaI-cut vector (dephosphorylated; commercially available from Amersham Corp., Arlington Heights, Ill.). The recombinant phages containing the fragment of interest were identified by Benton & Davis (1977, *Science* 196:180) screening procedure using radiolabeled oligonucleotide #13 as a probe. These recombinant clones were grown up to obtain sufficient quantities of single-stranded DNA for sequencing and were then sequenced by the dideoxy chain termination method (Sanger, et al., ibid.)

The hybridization conditions when long, randomly-labeled DNA probes were used were 5× SSCP, 2×

Denhardt's, 2 mM EDTA, 0.05% sodium pyrophosphate, 0.1% sodium dodecyl sulfate (SDS), 250 μg/ml of herring sperm DNA (non-specific competitor), pH 8.0. Hybridization was carried out at 65° C. and blots or filters were washed at 65° C. in 0.1× SSCP and 0.1% SDS. The hybridization conditions for shorter, oligonucletide probes were 6× SSCP, 2× Denhardt's, 2 mM EDTA, 0.05% sodium pyrophosphate, 0.1% SDS, 100 μg/ml yeast tRNA (non-specific competitor), pH 8.0. The temperature of hybridization and the conditions for washing blots and filters were individually adjusted for the GC content of each oligonucleotide (Maniatis et al., ibid.).

EXAMPLE 5

Expression of Genes Encoding SN-CNTF in Animal Cells

Animal-cell expression of SN-CNTF requires the following steps:

a. Construction of an expression vector;

b. Choice of a host cell line;

c. Introduction of the expression vector into host cells; and d. Manipulation of recombinant host cells to increase expression levels of SN-CNTF.

(a) SN-CNTF expression vectors designed for use in animal cells can be of several types including strong constitutive expression constructs, inducible gene constructs, as well as those designed for expression in particular cell types. In all cases, promoters and other gene regulatory regions such as enhancers (inducible or not) and polyadenylation signals are placed in the appropriate location in relation to the cDNA sequences in plasmid-based vectors. Two examples of such constructs follow: (1) A construct using a strong constitutive promoter region should be made using the simian virus 40 (SV4) gene control signals in an arrangement such as that found in the plasmid pSV2CAT as described by Gorman et al. in Mol. Cel. Biol. 2:1044–1051, 1982, specifically incorporated herein by reference. This plasmid should be manipulated in such as way as to substitute the SN-CNTF cDNA for the chloramphenicol acetyltransferase (CAT) coding sequences using standard molecular biological techniques (Maniatis et al., supra). (2) An inducible gene construct should be made utilizing the plasmid PMK which contains the mouse metallothionein (MT-1) promoter region (Brinster et al., Cell 27:228–231, 1981). This plasmid can be used as a starting material and should be manipulated to yield a metal-inducible gene construct.

(b) A number of animal cell lines should be used to express SN-CNTF using the vectors described above to produce active protein. Two potential cell lines that have been well characterized for their ability to promote foreign gene expression are mouse Ltk⁻ and Chinese hamster ovary (CHO) dhfr⁻ cells, although expression of SN-CNTF is not limited to these cell lines.

Animal cell lines that can be used for expression in addition to those mentioned above include the monkey kidney cell COS-7, which is useful for transient expression, and the human embryonic kidney cell 293.

(c) Vector DNA should be introduced into these cell lines using any of a number of gene-transfer techniques. The method employed here involves the calcium phosphate-DNA precipitation technique described by S. L. Graham and A. S. van der Eb (Virology 52:456–467, 1973) in which the expression vector for SN-CNTF is co-precipitated with a second expression vector encoding a selectable marker. In the case of Ltk⁻ cell transfection, the selectable marker is a thymidine kinase gene and the selection is as described by Wigler et al. in Cell 16:L777–785, 1979 and in the case of CHO dhfr⁻ cells, the selectable marker is dihydrofolate reductase (DHFR) whose selection is as described by Ringold et al. in J. Mol. Appl. Genet. 1:165–175, 1981.

(d) Cells that express the SN-CNTF gene constructs should then be grown under conditions that will increase the levels of production of SN-CNTF. Cells carrying the metallothionein promoter constructs can now be grown in the presence of heavy metals such as cadmium which will lead to a 5 fold increased utilization of the MT-1 promoter (Mayo et al., Cell 29:99–108) subsequently leading to a comparable increase in SN-CNTF protein levels. Cells containing SN-CNTF expression vectors (either SV40- or MT-1-based) along with a DHFR expression vector can be taken through the gene amplification protocol described by Ringold et al. in J. Mol. Apl. Genet. 1:165–175, 1981, using methotrexate, a competitive antagonist of DHFR. This leads to more copies of the DHFR genes present in the cells and, concomitantly, increased copies of the SN-CNTF genes which, in turn, can lead to more SN-CNTF protein being produced by the cells.

Figure 13:
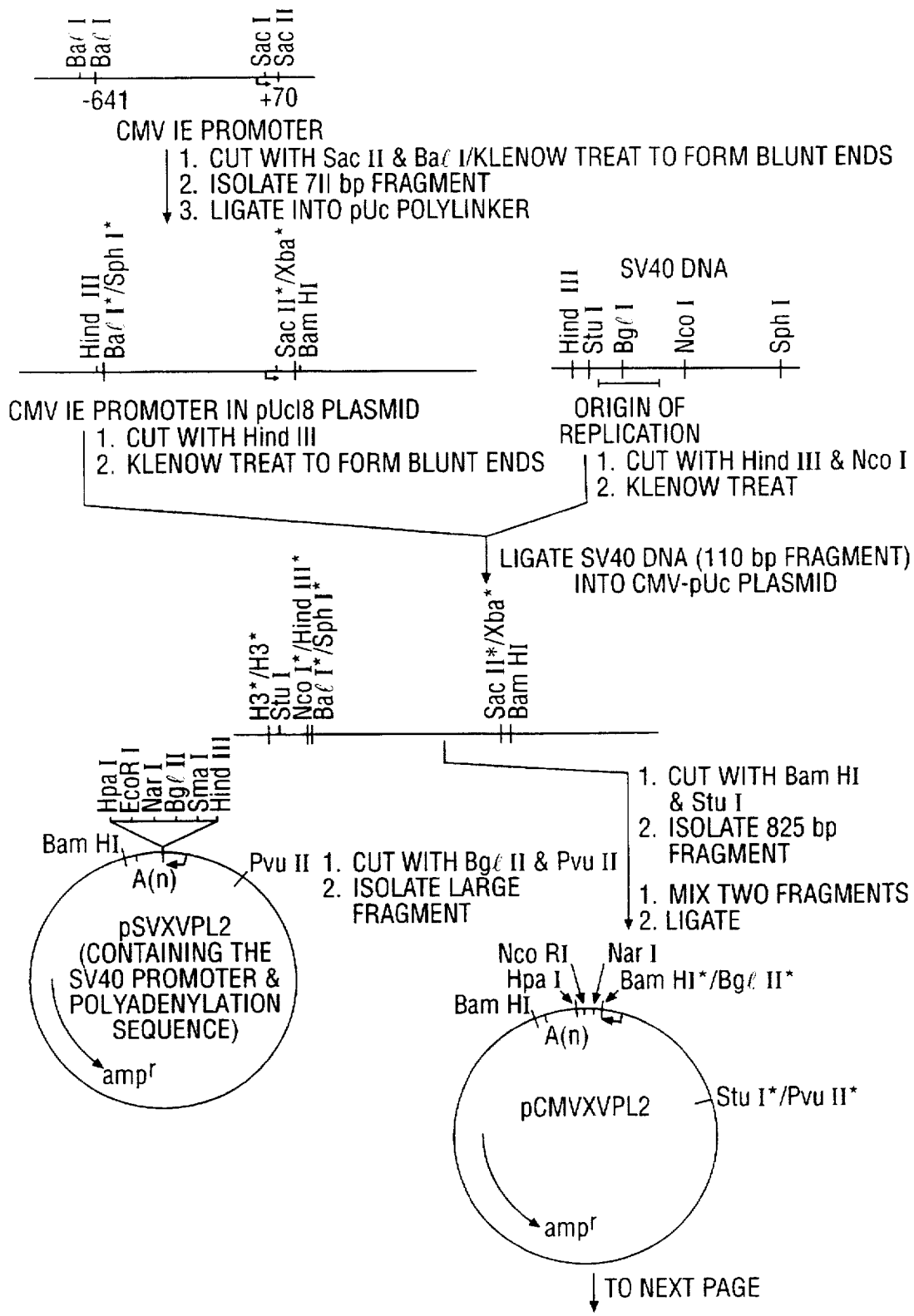
FIG. 13 depicts the construction of the pCMVXVPL2 expression vector.

An additional expression vector, pCMVXVPL2, was utilized to express the coding sequence for rabbit CNTF transiently in COS-7 cells. This plasmid vector contains the cytomegalovirus (CMV) immediate early promoter and enhancer as described by Boshart et al. (Cell 41:521–530, 1985). This plasmid can be constructed as shown in FIG. 13. The polyadenylation signal is provided by simian virus 40 (SV40) sequences (map coordinates 2589–2452; see Reddy et al., Science 200:494–502, 1978). The SV40 origin of replication is included in this plasmid to facilitate its use in COS cells for transient expression assays.

Rabbit SN-CNTF was transiently expressed in COS-7 cells as follows: The 1.5 kb Eco RI restriction fragment of a rabbit sciatic nerve cDNA clone containing the entire coding region for rabbit SN-CNTF (Example 4) was subcloned into the Eco RI-cut expression vector pCMVSVPL2. A single clone was selected which gave restriction fragments, after digestion with Sac I and Bam HI, that were of the size predicted for insertion of the 1.5 kb fragment into the vector in the correct orientation for CNTF expression. Plasmid DNA from this construct was prepared by the method of alkaline lysis followed by CsCl density centrifugation (Maniatis et al., ibid.). This DNA was transfected into COS-7 cells by the method of Sompayrac and Danna (Proc. Natl. Acad. Sci., U.S.A. 78:7575–7578, 1981). As a control, equivalent COS cell structure cultures were transfected with plasmid vector DNA with no insert.

Forty-eight hours after transfection, the overlying medium and cell pellets were harvested. Cell pellets were extracted by brief sonication on ice in 20 mM sodium phosphate, pH 6.7 containing 1 mM EDTA, 0.1 mM PMSF, and 0.1 μM pepstatin. Serial dilutions of both the cell extract and the overlying medium from each culture were assayed for activity in the ciliary ganglion survival assay.

The cell extracts from cultures transfected with vector containing the CNTF cDNA fragment had a titer of ca. 15,000 TU/ml in the bioassay and approximately 50 ng/ml of CNTF as determined by Western blot analysis. Neither the cell extracts from cultures transfected with vector alone nor the overlying medium from any cultures displayed any detectable bioactivity or CNTF protein by Western blot analysis. This result clearly demonstrates that the CNTF cDNA we have cloned encodes a protein with the anticipated bioactivity of authentic SN-CNTF.

EXAMPLE 6

Purification of SN-CNTF from Recombinant Animal Cells

Since SN-CNTF is expected to be synthesized by cells like the natural material, it is anticipated that the method described above for purification of the natural protein will allow similar purification and characterization of the recombinant protein.

It will be apparent to those skilled in the art that various modifications and variations can be made in the processes and products of the present invention. Thus, it is intended that the present invention cover the modifications and variations of this invention provided they come within the scope of the appended claims and their equivalents. Also, the term SN-CNTF is intended to encompass all origins of species, unless the term is immediately preceded by a specific origin of species.

EXAMPLE 7

Production of Recombinant Human DNTF

As one embodiment of the present invention, a system for producing recombinant human CNTF was established in the bacterium *Escherichia coli*. Two alternative methods for constructing the DNA to be expressed and two different expression vectors were used. All of these variant expression systems produce soluble CNTF protein in high yield that is biologically active in the bacterial cell extract. The methods for establishing these production systems are described below. Please note in what follows that the position of a feature given in brackets (e.g., [233]) refers to the number of bases at which the feature begins downstream of the A [1] in the initial ATG codon in the human coding sequence for CNTF (FIG. 12).

1. Preparation of DNA for the Expression of CNTF

Figure 14:
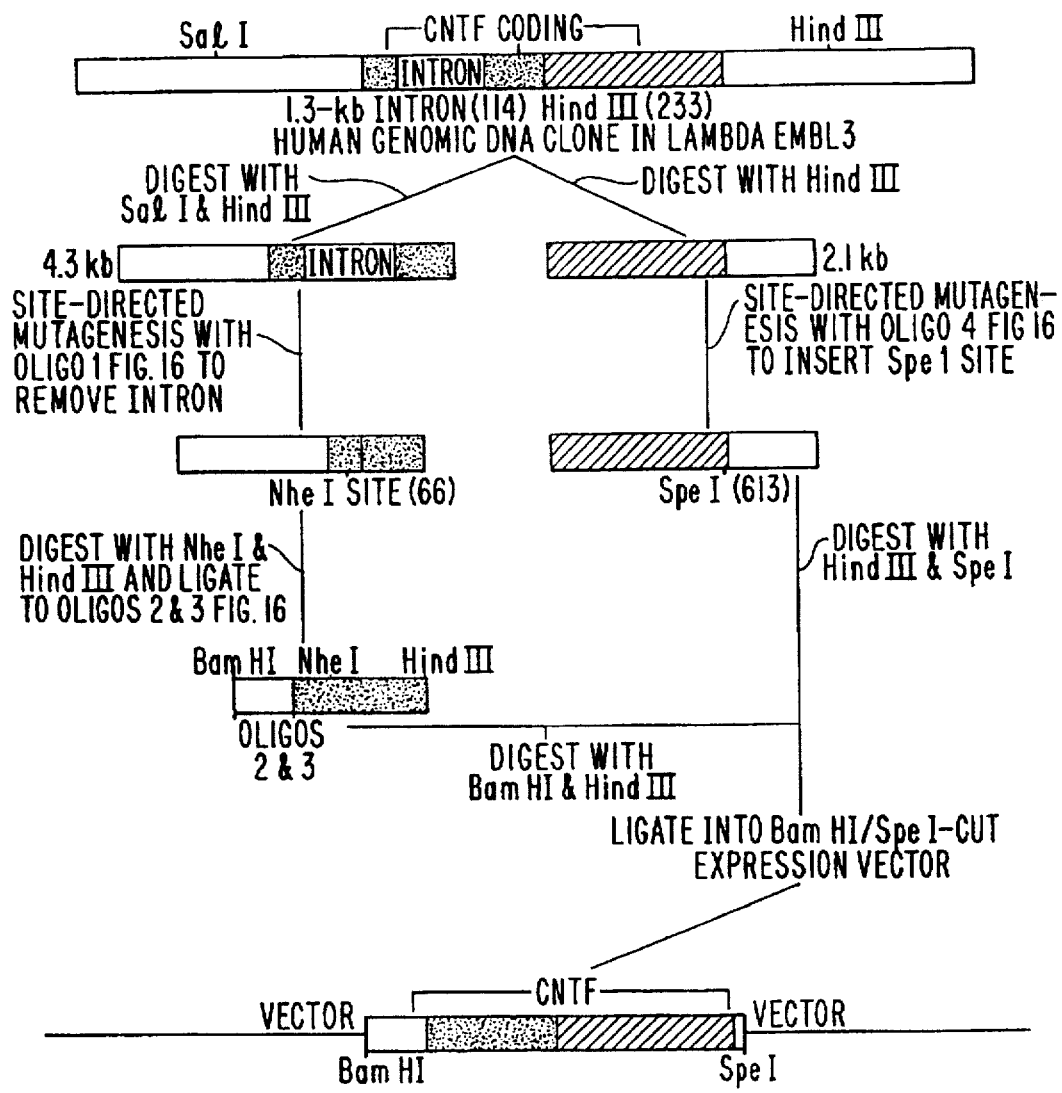
FIG. 14 depicts the methods used to construct CNTF-Syn1/3 for expression of CNTF. The drawing is representative and not to sale. See Example 7 for experimental details.

Strategy 1 for constructing the 5' End FIG. 14): The human genomic DNA clone for CNTF in phage lambda EMBL3 from Example 4 was digested with the restriction enzymes Sal I and Hind III and a 4.3-kb fragment was gel purified that contained the CNTF coding sequences upstream of the Hind III site [233]. This 4.3-kb fragment also contains a single, approximately 1.3-kb intron [114–115] in the coding sequence. To allow expression in bacterial cells, the intron was removed by site-directed mutagenesis in vitro using a synthetic oligonucleotide as described by J. A. McClary, F. Whitney, J. Geisselsoder (1989) *Biotechniques* 7:272–289.

A. Intron deletion by site-directed mutagenesis using phagemid vector and genetic selection Site-directed mutagenesis was carried out to delete the ca. 1.3-kb intron in the 4.3-kb Sal I/Hind III DNA fragment subcloned into a phagemid vector, Bluescript SK M13(−) (Stratagene). This vector was chosen since it can accept the large size (ca. 4.3 kb) of the SalI/HindIII insert. Phagemid vectors are plasmid vectors containing the bacteriophage f1 intergenic region that allows rescue as single-stranded DNA. In addition, phagemid vectors have a number of advantages over the single-stranded M13 bacteriophage vectors. Since the phagemids are less than half the size of M13 vectors, which prefer inserts with sizes less than ca. 2.3 kb, larger inserts can be subcloned more easily into phagemids and chances of spontaneous deletions are reduced. Another advantage of phagemids is that the inserts can be sequenced directly from double-stranded supercoiled DNA, thereby simplifying their characterization.

Mutagenesis was carried out using the Muta-Gene In Vitro Mutagenesis kit from BioRad. The host cell for template preparation from mutagenesis is the *E. coli* strain CJ236 (Genotype: dut, ung, thi, rel Al, pCJ105 [cap']). CJ236 carries a F'-factor selectable by chloramphenicol, thus allowing for rescue of single-stranded phagemid DNA using an appropriate helper phage. R408 used in the present work. The rescued single-stranded phagemid DNA is partially substituted with uracil, due to the dut (dUTPase) and ung (uracil N-glycosylase) mutations in CJ236. Template DNA, substituted with uracil and used for mutagenesis, is selectively destroyed when transformed into host cells that contain wild-type ung loci, such as DH5α in this case, thus allowing preferential replication of the newly synthesized mutated DNA.

To perform mutagenesis, the gel-purified 4.3-kb SalI/HindIII fragment was ligated into SalI/HindIII digested and gel purified Bluescript SK M13(−). The ligated DNA was introduced into CJ236 made competent by Hanahan's method as described in *J. Mol. Biol.* 166:557 (1983). Transformants were selected on plates containing 50 μg/ml ampicillin (to select for the phagemid) and 30 μg/ml chloramphenicol (to select for retention of the F'-factor). Transformants were checked for the presence of the correct insert by restriction enzyme analysis of transformant DNAs. A transformant carrying the correct insert (pSHM-D19) was used in subsequent mutagenesis experiment.

Single-stranded template from pSHM-D19 was rescued using phage R408 as helper phage. CJ236 containing pSHM-D19 was grown in Luria broth containing ampicillin (50 μg/ml) and chloramphenicol (30 μg/ml) to an $A_{600}$ of ca. 0.3. Cells were infected with R408 helper phage at a multiplicity of infection of 20, then shaken at 37° C. for between 8–14 hours. Single-stranded template was extracted from rescued phagemids.

Site-directed intron deletion mutagenesis was performed using a 71-base oligonucleotide (Oligonucleotide 1 in FIG. 16). Oligonucleotide 1 has bases 1–30 complementary to the coding strand immediately downstream (3') and bases 31–71 complementary to the coding strand immediately upstream (5') of the intron to be deleted from the CNTF genomic DNA. For use in mutagenesis reactions, the oligonucleotide was phosphorylated using T4 polynucleotide kinase. Mutagenesis reactions using the BioRad MutaGene kit was performed according to manufacturer's specifications, except that DNA from mutagenesis reactions was used to transform *E. coli* strain DH5α. Deletion mutants were characterized by restriction enzyme mapping of the DNAs and DNA sequencing of double-stranded DNAs from mutants with the appropriate restriction maps. pMCN-2a was a correctly-deleted intron-less mutant in the Bluescript phagemid.

B. Reconstruction of the 5' end of the CNTF gene for expression

The 5' end of the CNTF coding sequence was reconstructed in order to make certain changes which do not alter the amino acid sequence coded for but which are likely to increase the efficiency of expression in bacteria. The partially overlapping, complementary oligonucleotides 2 and 3 (FIG. 16) were synthesized, gel purified, and annealed together. Oligonucleotide 2 codes for the amino acids present in human CNTF upstream of the Nhe I site [66]. The coding sequence of oligonucleotide 2 contains several bases that differ from those present in the human gene (compare FIGS. 12 and 16). These changes were made either to alter the human codon usage to that used preferentially *E. coli* (according to deBoer and Kastelein in *From Gene to Pro-* tein: *Steps Dictating the Maximal Level of Gene Expression* (1986) Davis and Rezinkoff, eds. pp. 225–283, Butterworths, NY) or to generate a Bgl II site (FIG. 16), put into the sequence for ease of subsequent genetic manipulations. Oligonucleotide 2 also codes for a translational coupler toward the 5'end (FIG. 16) to promote effective translation. Annealed oligonucleotides 2 and 3 have a Bam HI overhang at the 5' end and a Nhe I overhang at the 3' end for ease of subsequent ligation and cloning (FIGS. 14 & 16). A restriction enzyme search of the DNA sequence of the human CNTF gene showed a unique Nhe I recognition sequence |66| (FIG. 12). Therefore, oligonucleotides 2 & 3 were designed with a Nhe I overhang to allow them to be joined to the remaining 3' fragment of the gene after digestion with Nhe I.

C. Joining of Oligonucleotides 2 & 3 to the intron-deleted coding sequences

Oligonucleotides 2 and 3, containing the rebuilt amino-terminus of the CNTF gene, were annealed together and ligated to Nhe I cut pMCN-2a. Ligated DNA was then digested with Bam HI and Hind III to release the DNA fragment referred to as CNTF-Syn1 which contains DNA sequences suitable for expression in *E. coli* and encoding human CNTF upstream of the Hind III site |233|.

Figure 15:
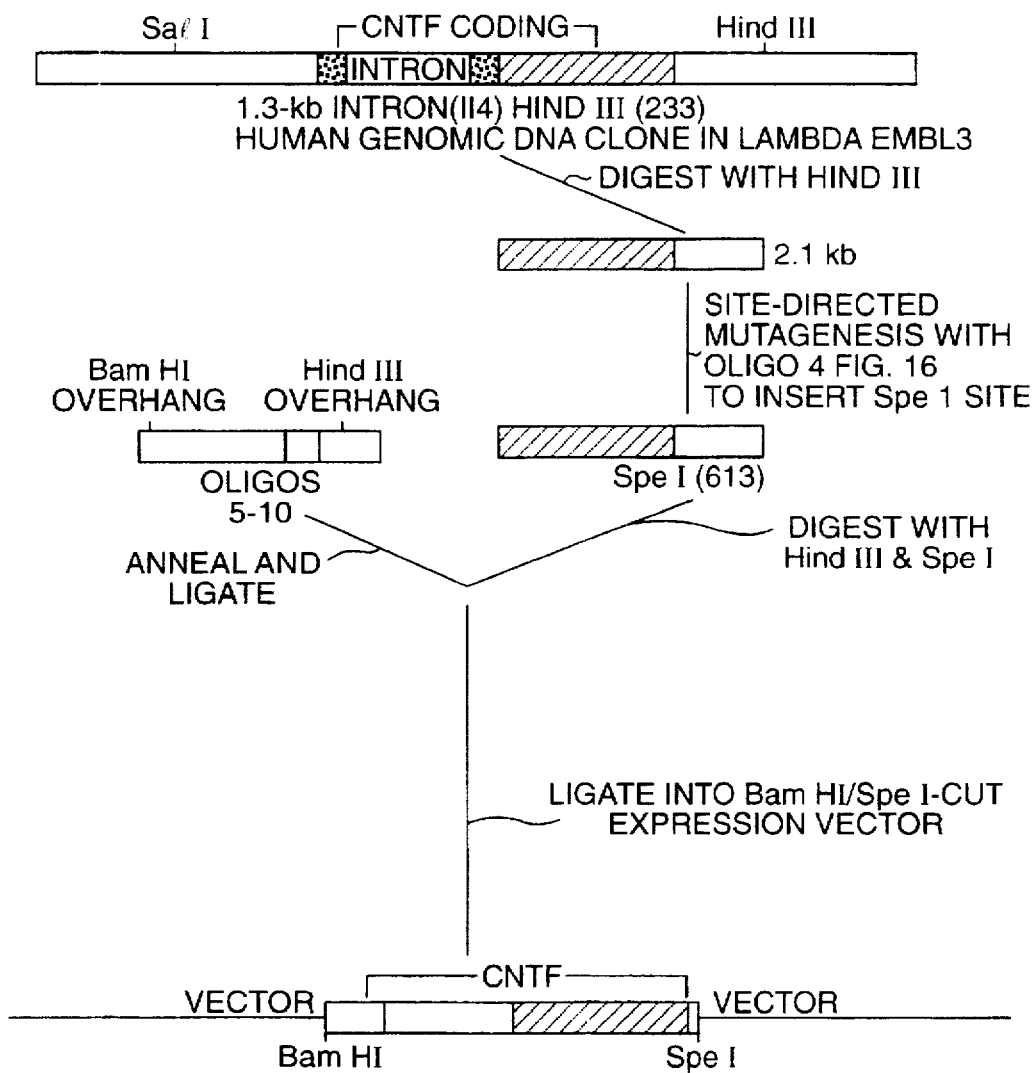
FIG. 15 depicts the methods used to construct CNTF-Syn2/3 for expression of CNTF. The drawing is representative and not to sale. See Example 7 for experimental details.
Figure 18:
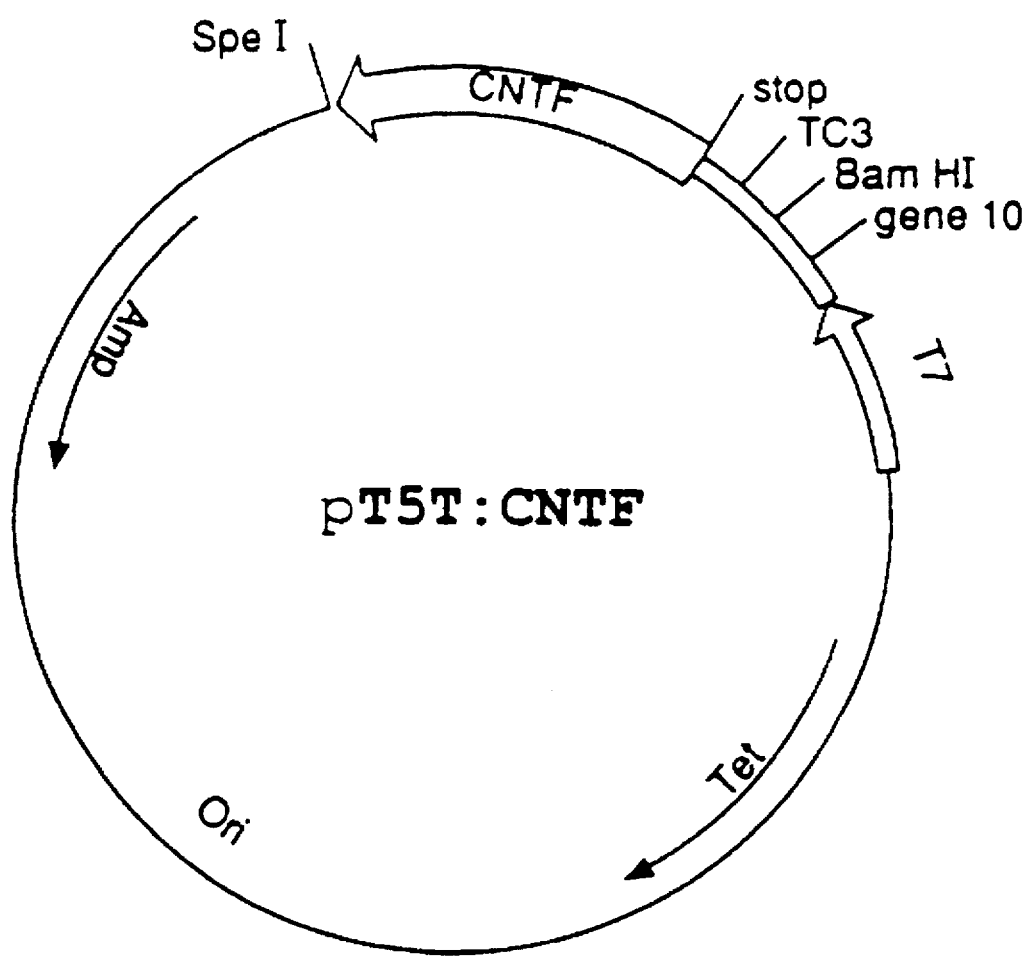
FIG. 18 depicts certain features of the pT5T bacterial expression vector containing a DNA insert suitable for expression of CNTF. The drawing is representative and not to scale. See Example 7 for experimental details.

CNTF-Syn3 to produce CNTF-Syn2/3 (FIG. 15) in order to construct two alternative DNA fragments each of which codes for human CNTF and has suitable modifications of the DNA sequence to promote efficient expression in *E. coli*. These DNA fragments were then expressed in *E. coli* after being subcloned into: (A) a bacterial expression vector, pT5T, based on the T7 phage promoter; or (B) a bacterial expression vector, pT3XI-2, based on a hybrid lactose and tryptophan operon promoter ('Tac').

2. Expression of CNTF using an expression vector based on the "T7 promoter" system (Please refer to FIG. 17 for features of the vector):

A. Description of pT5T

The T7 promoter based expression vector pT5T is essentially the same as pJU1003 described by Squires, et. al., *J. Biol. Chem.* (1988) 263:16297–16302, except that there is a short stretch of DNA between the unique Bgl II site 5' to the T7 promoter and the Cla I site in the tetracycline resistance gene. The sequence of this DNA is:

```
ATCGATGATA AGCTGTCAAA CATGAGAATT GAGCTCCCCG GAGATCCTTA GCGAAAGCTA
Cla I

AGGATTTTTT TTAGATCT
         Bgl II
```

Strategy 2 for constructing the 5' End (FIG. 15): An alternative strategy was carried out in which the intron was not removed by site-directed mutagenesis but rather an entirely synthetic DNA sequence was prepared coding for CNTF upstream of the Hind III site |233|, but without the intron. To form this synthetic DNA construct, oligonucleotides 5 through 10 in FIG. 17 were synthesized. The following oligonucleotides were designed to form partially overlapping, double-stranded pairs: 5&6, 7&8, 9&10. Each double-stranded pair contains single-stranded overhangs designed to allow ligation together in the order 5&6–7&8–9&10. The oligonucleotides were gel purified, annealed, and ligated together into a single 261 base pair double-stranded DNA oligonucleotide, referred to as CNTF-Syn2. This synthetic DNA also contained: (1) altered codons to fit *E. coli* codon usage preferences (compare FIGS. 12 and 17); (2) the 5' translational coupler used above (FIG. 16 and 17); and (3) a 5' Bam HI overhang and a 3' Hind III overhang to facilitate ligation and cloning (FIG. 17).

Preparation of the 3' End of the Expression Construct (FIGS. 14 or 15): The human genomic DNA CNTF clone in phage lambda EMBL3 from Example 4 was cut with the restriction enzyme Hind III and a 2.1-kb fragment was gel purified containing the CNTF coding sequences downstream of the Hind III site |233|. This 2.1-kb fragment was cloned into Hind III-cut plasmid pEMBL8 (Dente et al., 1983, *Nucleic Acids Res.* 11:1645). A Spe I site |613| was inserted into the 2.1-kb insert DNA by oligonucleotide directed mutagenesis 13 base pairs downstream of the stop codon ending the CNTF sequence using the synthetic Oligonucleotide 4 (FIG. 16). The mutated plasmid was cut with Hind III and Spe I to release the downstream coding fragment which was gel purified and is referred to as CNTF-Syn3 (containing the coding sequences for human CNTF downstream of the Hind III site |233|).

Preparation of the Complete Expression Construct

CNTF-Syn1 was ligated to CNTF-Syn3 to produce CNTF-Syn1/3 (FIG. 14) and CNTF-Syn2 was ligated to B. Construction of the complete expression vector The gel-purified vector was linearized with Bam HI and Spe I restriction enzymes. CNTF-Syn1/3 was mixed with the linearized vector and ligated to form the expression construct pT5T:CNTF-Syn1/3. (See FIG. 14 for the general outline of vector construction).

C. Expression of recombinant human CNTF in *E. coli* pT5T:CNTF-Syn1/3 was transformed into the *E. coli* strain BL21(DE3) for expression. This strain described in Studier and Moffat *J. Mol. Biol.* (1986) 189:113–130, contains the T7 RNA polymerase gene under control of the IPTG inducible lac promoter on a nonexcisable lysogenic lambda bacteriophage. Of 10 transformants screened, two clones were found to be expressing an IPTG-inducible protein migrating at a molecular weight in the range appropriate of CNTF (ca. 24 kD). These two clones have been designated as pT5T:CNTF-Syn1/3-5a and 5c. DNA sequencing of pT5T:CNTF-Syn1/3-5a and 5c confirmed that the sequences of the recombinants were correct.

High level expression of recombinant CNTF was achieved by growing the cells in Luria broth with 15 µg/ml tetracycline up to a cell density corresponding to an $A_{600}$ of 0.5–0.8. Cells were grown for 1.5–4 hours either without IPTG ("uninduced") or IPTG was added to a final concentration of 1.0 mM ("induced"). IPTG (isopropylβ-D-thiogalatopyranoside) is an inducer of the lac operon whose presence should result in indirect activation of the expression vector's T7 polymerase and increased levels of expression of CNTF.

Figure 20:
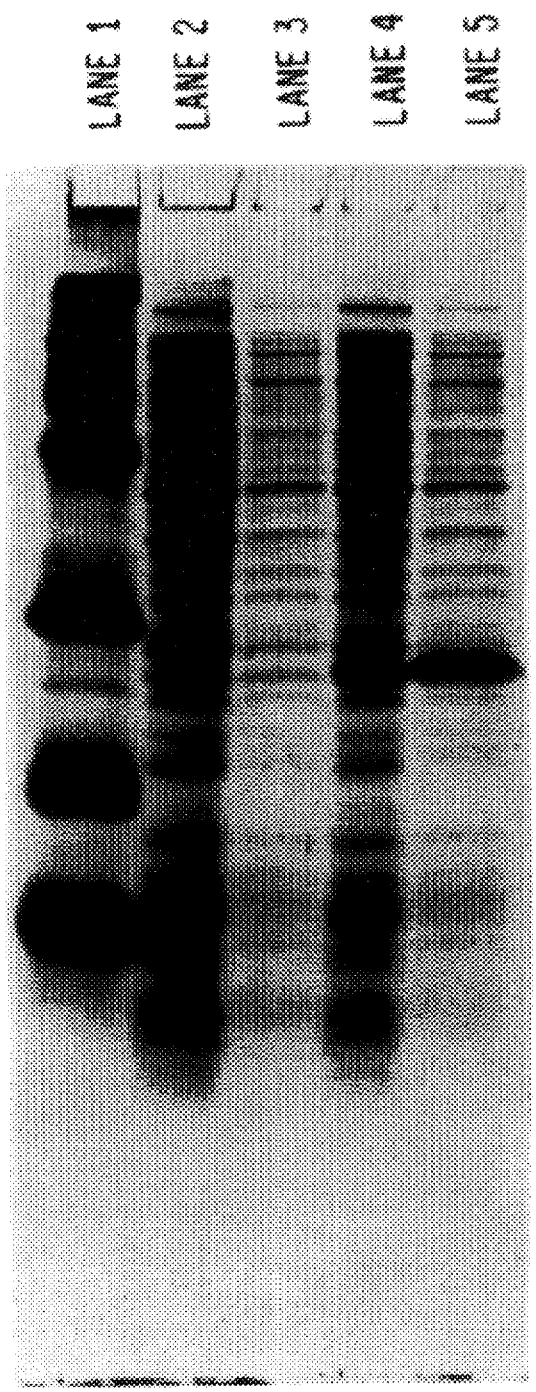
FIG. 20 depicts a reducing SDS polyacrylamide gel in which extracts of cells transformed with various expression constructs were electrophoresed and stained with Coomassie Brilliant Blue.
Figure 21:
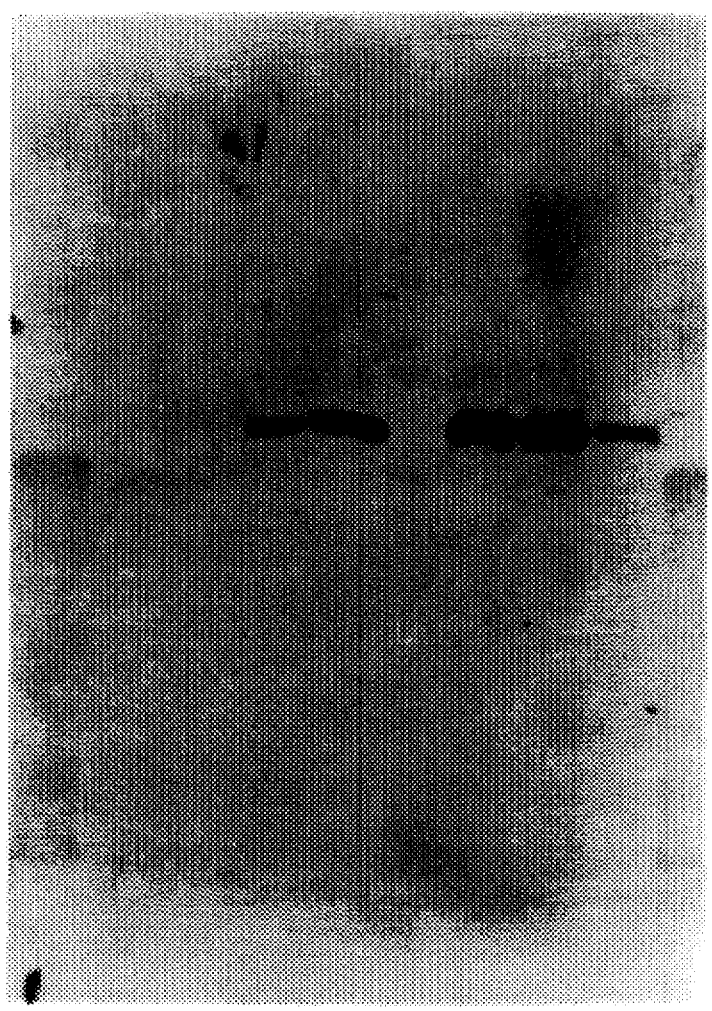
FIG. 21 depicts a reducing SDS polyacrylamide gel in which extracts of cells transformed with various expression constructs were electrophoresed and immunoblotted with affinity-purified anti-CNTF peptide A antibody.

D. Analysis of expressed protein by SDS polyacrylamide gel electrophoresis followed by staining with Coomassie stain or immunoblotting Cells were harvested by brief centrifugation and dissolved directly in SDS-polyacrylamide gel sample buffer (0.025% bromphenol blue, 10% glycerol, 1% β-mercaptoethanol, 2% SDS, 0.0625M Tris-HCl, pH 6.8) and boiled for 2 min (FIG. 20 and FIG. 21). In cells transformed with pT5T:CNTF- Syn1.3-5a and induced with IPTG for 2 hours (lane 5, FIG. 20) there is a band darkly stained with Coomassie stain running at the position expected of CNTF (ca. 24 kD). If the cells are grown without IPTG (lane 4, FIG. 20) there is much less of this band, as expected for a protein whose expression is under control of the lac operon. Cells transformed with pT5T vector without a CNTF insert do not show this band either induced (lane 3, FIG. 20) or uninduced (lane 2, FIG. 20). Lane 1 contains molecular weight standards.

An identical SDS-polyacrylamide gel was transferred to nitrocellulose and immunoblotted with affinity-purified antibodies to CNTF peptide A (E-S-Y-V-K-H-Q-G-L-N-K-N). In cells transformed with pT5T:CNTF-Syn1.3-5a and induced with IPTG for 2 hours (lane 5, FIG. 21) there is a dense band recognized by the affinity-purified antibodies to CNTF peptide A and running at the position expected of CNTF (ca. 24 kD). If the cells are grown without IPTG (lane 4, FIG. 21) there is much less of this band. Cells transformed with pT5T vector without a CNTF insert do not show this band either induced (lane 3, FIG. 20) or uninduced (lane 2, FIG. 20). Lane 1 contains molecular weight standards.

In addition, cells transformed with pT5T:CNTF-Syn1,3-5a and induced with IPTG for 2 hours were broken open by passage three times through a French pressure cell. An aliquot of the crude cell lysate was separated into supernatant and pellet fractions by centrifugation at 20,000 rpm in JA-20 rotor (Beckman) for 15 min. Aliquots of the crude lysate, supernatant, and pellet fractions, representing the same amount of starting cell suspension, were also run on the same SDS polyacrylamide gel, transferred to nitrocellulose and immunoblotted with affinity-purified anti-peptide A antibodies. The lysate supernatant (lane 8, FIG. 21) contained much more immunoreactive CNTF than did the lysate pellet (lane 9, FIG. 21), the supernatant CNTF level was comparable to that in the unfractionated lysate (lane 7, FIG. 21).

E. Bioactivity of expressed CNTF

Figure 22:
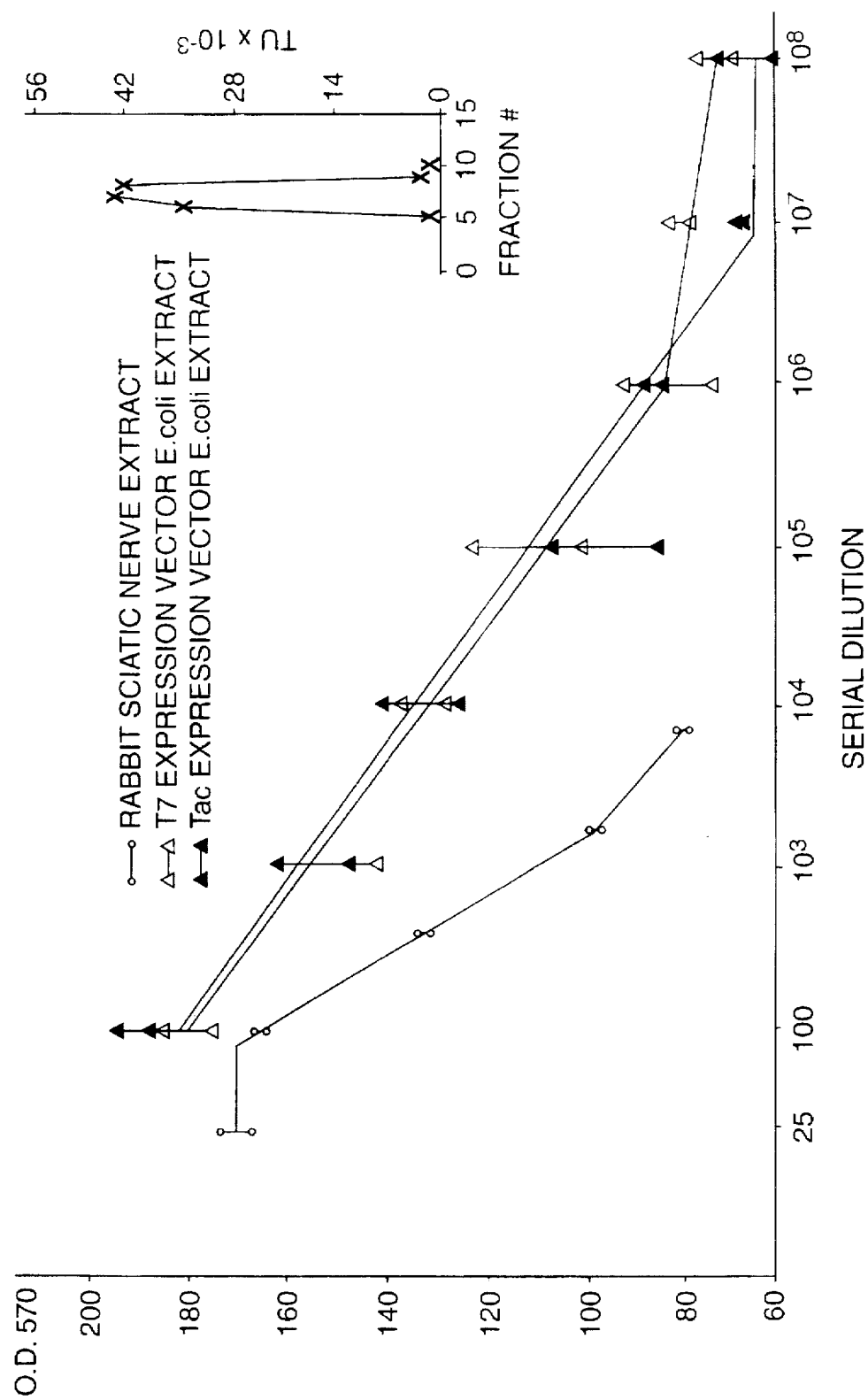
FIG. 22 depicts the bioassay of serial dilutions of supernatants from bacterial cells expressing pT5T:CNTF-Syn1/3 or pT3XI-2:CNTF-Syn2/3. The inset depicts the bioassay of extracted slices from a reducing SDS polyacrylamide gel of the pT5T:CNTF-Syn1/3 supernatant in the region of the gel immediately above and below 24 kD.

Cells harvested by brief centrifugation were resuspended in 20 mM Tris-HCl, pH 8.2 at 1/35 the original volume of cell suspension, broken open by passage through a French pressure cell three times, and the crude cell lysate separated into a supernatant and pellet fractions by centrifugation at 20,000 rpm in JA-20 rotor (Beckman) for 15 min. Serial dilutions of the cell supernatant fraction were assayed for their ability to promote the survival of ciliary ganglion nerve cells (as described in Example 1). The supernatant showed significant bioactivity out to a dilution of 1:1,000,000 (FIG. 22). The specific activity of recombinant human CNTF was estimated to be approximately 275 TU/ng, based on bioactivity and on the amount of CNTF protein estimated from immunoblots. This specific activity is about twice the specific activity of the purified rabbit CNTF protein, indicating that the recombinant CNTF is biologically active in the bacterial cell extract. Lysates of cells transformed with pT5T without a CNTF insert exhibited no detectable bioactivity.

The supernatant was also electrophoresed on a 15% polyacrylamide reducing SDS gel and sliced into 1 mm wide slices that were extracted overnight in cell culture medium at 4° C. with rocking and bioassayed as described in Example 1. The inset to FIG. 22 illustrates that there is a peak of bioactivity at fractions corresponding to 24 kD as expected for CNTF.

F. Amino acid sequence of expressed CNTF

The region around 24 kD was cut out of an SDS polyacrylamide gel similar to that run for FIG. 20 but without Coomassie staining. This material was sequenced by Edman degradation in an Applied Biosystems Protein Sequencer (as described in Example 2). The following amino acid sequence was obtained: AFTEHSPLTPHRRDL|!|S . . . The question mark corresponds to a C in the human sequence (FIG. 12) which cannot be detected by this method. This sequence corresponds to that expected from human CNTF (FIG. 12) and provides additional evidence that CNTF is being properly expressed. It also indicates that the amino-terminal methionine is removed during expression, leaving the alanine as the amino-terminal amino acid in the expressed protein.

The above results demonstrate that immunologically cross-reactive CNTF has been expressed at high levels in a biologically active form, most of which is soluble after lysis of the bacterial cells.

Figure 19:
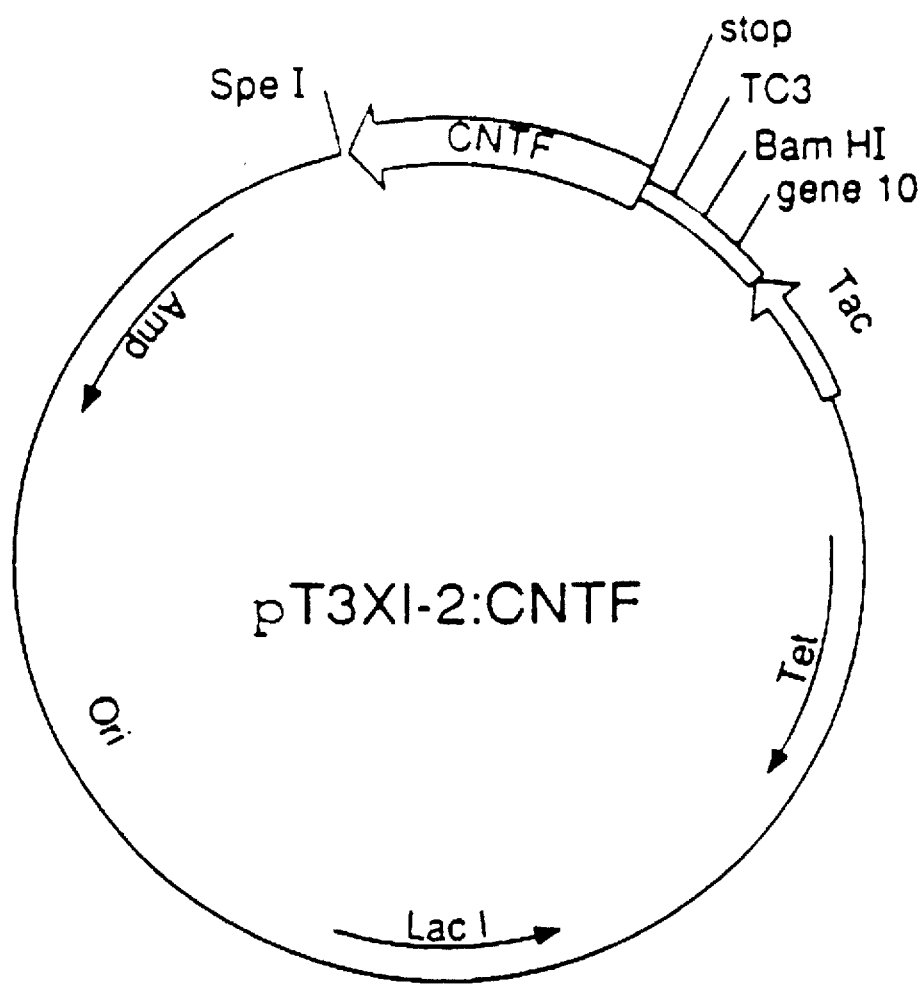
FIG. 19 depicts certain features of the pT3XI-2 bacterial expression vector containing a DNA insert suitable for expression of CNTF. The drawing is representative and not to scale. See Example 7 for experimental details.

3. Expression of CNTF using an expression vector based on a hybrid lactose and tryptophan operon promoter ('Tac') system See FIG. 19 for features of the vector):

A. Description of pT3XI-2 (modification of pKK223-3)

The starting plasmid for this construction was plasmid pKK223-3 purchased from Pharmacia. Plasmid pKK223-3 carries a partial gene for tetracycline resistance. This nonfunctional gene was replaced by a complete tetracycline resistance gene carried on plasmid pBR322. Plasmid pKK223-3 was digested completely with Sph I and partially with Bam HI. A 4.4 kilobase pair fragment was gel purified and combined with a synthetic adaptor with the sequence:

5'  GATCTAGAATTGTCATGTTTGACAGCTTATCAT       3'

3'           ATCTTAACAGTACAAACTGTCGAATAGTAGC  5' and a 539 base pair fragment of DNA from a Cla I, Sph I digest of the tetracycline resistance gene of pBR322 (PL Biochemicals, 27-4891-01). The resulting plasmid was designated pCJ1.

Next a Xho I linker purchased from New England Biolabs was inserted into plasmid pCJ1's Pvu II site to form plasmid pCJX-1. This insertion disrupts the rop gene which controls plasmid copy number. An Eco RI fragment containing the lac 1 gene was purified from plasmid pMC9 [Calos, et al., Proc. Natl. Acad. Sci. U.S.A. (1983), 80:3015–3019] then inserted into the Xho I site with Xho I to Eco RI adapters having the sequence:

5'   TCGAGTCTAGA         3'

3'             CAGATCTTTAA     5'

The polylinker sequence between the Eco RI and Pst I sites in plasmid pKK223-3 was next replaced with a polylinker sequence shown here:

5' AATTCCCGGG TACCAGATCT GAGCTCACTA GTCTGCA 3'

3'     GGGCCC ATGGTCTAGA CTCGAGTGAT CAG       5'

The plasmid vector so obtained is designated pCJXI-1.

Finally, the tetracycline resistance gene was replaced with a similar gene which had the recognition sites for restriction enzymes Hind III, Bam HI, and Sal I destroyed by bisulfite mutagenesis. The following procedure was used to mutate the tetracycline resistance gene of pBR322. Plasmid pBR322 was cut with Hind III, then mutagenized with sodium bisulfite [Shortle and Nathans, Proc. Natl. Acad. Sci.

U.S.A. (1978) 5:2170–2174]. The mutagenized DNA was ligated to form circular DNA, then cut with Hind III to linearize any plasmid that escaped mutagenesis. *E. coli* JM109 [Yanisch-Perron, et al., *Gene* (1985) 33:103–119] was transformed with the plasmid, then plated on selective media. Plasmids were isolated from tetracycline resistance colonies and checked for loss of the Hind III site in the tetracycline resistance gene. The successfully mutated plasmid was designated pT1. A similar procedure was followed to mutagenize the Bam HI site in pT1, yielding plasmid pT2. Plasmid pT2 in turn was mutagenized to remove the Sal I site, forming plasmid pT3. A Cla I/Bsm I fragment of pT3 carrying the mutated tetracycline resistance gene was isolated and used to replace the homologous fragment of pCJXI-1 to form pT3XI-2. The mutated tetracycline resistance gene still encodes a functional protein.

B. Formation of pT3XI-2-φ10TC3FGFsyn (preparing the tac promoter vector for CNTF)

Initially a "gene" for basic Fibroblast Growth Factor (bFGF) was synthesized. This "gene" codes for the same sequence as that reported for FGF by Sommer et al. (1987 *Biochem. Biophys. Res. Commun.* 141:67) but uses the codons that are found preferentially in highly expressed genes in *E. coli*. The structure of this gene is such that the coding portion is preceded by a sequence (see Squires, et al., 1988, ibid.) to ensure efficient initiation of translation.

The FGF synthetic gene was first inserted into M13mp18 between the Eco RI and Hind III sites and sequenced. The structure of this gene is:

Relevant features of the gene are highlighted.

It was then isolated by digestion with Bam HI and Hind III and inserted into Bam HI/Hind III-cut pJU1003 (Squires, et al., 1988, ibid.) yielding pJU1003-synFGF. This plasmid was cut with Xba I and Hind III and the Xba I/Hind III fragment carrying the FGF gene was isolated. This fragment was ligated into pT3XI-2 cut with Eco RI and Hind III, using an Eco RI-Xba I linker:

5' p AAT TCC ACA ACG GTT TCC CT         5'

3'         GG TGT TGC CAA AGG GAG ATCp 5'

The new plasmid is designated pT3XI-2-φ10TC3FGFsyn.

C. Inserting CNTF expression constructs into the Tac promoter vector pT3XI-2-φ10TC3FGFsyn was cut with Bam HI and Spe I, which resulted in the linearization of the 7.4 kb expression vector and the release of the ca. 0.5-kb FGF DNA fragment. In separate reactions, CNTF-Syn1/3 and CNTF-Syn2/3 were ligated into the gel purified Bam HI/Spe I-cut vector DNA fragment, resulting in the plasmids pT3XI-2:CNTF-Syn1/3 and pT3XI-2:CNTF-Syn2/3.

D. Expression in *E. coli*.

pT3XI-2:CNTF-Syn1/3 was transformed into a phage-resistant *E. coli* K-strain, JM107. Fourteen transformants were grown up and analyzed for CNTF expression by SDS polyacrylamide gel electrophoresis and staining with Coo-

```
         AATTCAGGA TCCGATCGTG GAGGATGATT AAATGGGTAC CATGGCTGCT GGCTCCATCA
         GTCCT AGGCTAGCAC CTCCTACTAA TTTACCCATG GTACCGACGA CCGAGGTAGT
EcoRI    BamHI          RBS                   FGFstart
                Translational Coupler 3

CTACCCTGCC GGCACTGCCG GAAGACGGTG GCTCCGGTGC TTTCCCGCCG GGCCACTTCA
GATGGGACGG CCGTGACGGC CTTCTGCCAC CGAGGCCACG AAAGGGCGGC CCGGTGAAGT

AAGACCCGAA ACGTCTGTAC TGTAAAAACG GTGGCTTCTT CCTGCGTATC CACCCGGATG
TTCTGGGCTT TGCAGACATG ACATTTTTGC CACCGAAGAA GGACGCATAG GTGGGCCTAC

GTCGTGTCGA CGGCGTACGT GAAAAAAGCG ACCCGCACA TCAAACTGCA GCTGCAGGCTG
CAGCACAGCT TGCCGCATGC ACTTTTTTCC TGGGCGTGT AGTTTGACGT CGACGTCCGAC

AAGAACGTG GTGTTGTATC TATCAAAGGC GTTTGCGCAA ACCGTTACCT GGCTATGAAAG
TTCTTGCAC CACAACATAG ATAGTTTCCG CAAACGCGTT TGGCAATGGA CCGATACTTTC

AAGACGGTC GTCTGCTGGC TAGCAAATGT GTAACTGACG AATGTTTCTT CTTCGAACGTC
TTCTGCCAG CAGACGACCG ATCGTTTACA CATTGACTGC TTACAAAGAA GAAGCTTGCAG

TGGAAAGCA ACAACTACAA CACCTACCGT TCTCGTAAAT ACACTTCTTG GTACGTTGCTC
ACCTTTCGT TGTTGATGTT GTGGATGGCA AGAGCATTTA TGTGAAGAAC CATGCAACGAG

TGAAACGTA CCGGCCAGTA CAAACTGGGT TCCAAAACTG GCCCGGGTCA GAAAGCAATCC
ACTTTGCAT GGCCGGTCAT GTTTGACCCA AGGTTTTGAC CGGGCCCAGT CTTTCGTTAGG

TGTTCCTGC CGATGAGCGC TAAATCTTAA ACTAGTA
ACAAGGACG GCTACTCGCG ATTTAGAATT TGATCATTCGA
                                FGFstop         HindIII
``` massie Brilliant Blue. Four transformants exhibited a darkly-stained band at the approximate position of CNTF. High level expression of recombinant CNTF was achieved by growing the cells in Luria broth with 15 µg/ml tetracycline up to a cell density corresponding to an $A_{600}$ of 0.8. IPTG was added to a final concentration of 1.0 mM and the cells were allowed to grow for two hours. These four transformants all exhibited about the same density of CNTF on both Coomassie-stained and immunoblotted gels. The apparent level of CNTF expression in these transformants, based on these gels, was about one-fourth that exhibited by pT5T:CNTF-Syn1/3-5a grown as previously described. Restriction mapping of the DNAs of these four transformants confirmed that they all carried the human CNTF gene.

PT3-XI-2:CNTF-Syn2/3 was transformed into the *E. coli* stain TG1 for expression. Transformants were selected by plating on Lb agar containing 15 µg/ml tetracycline. Four transformants, pT3XI-2:CNTF-Syn2/3-A, -B, -C, -D, were selected, grown up, and confirmed by restriction enzyme mapping. One transformant, pT3XI-2:CNTF-Syn2/3-A, was selected for further study. This transformant was grown overnight in 500 ml 2XYT broth plus 10 µg/ml tetracycline and 1 mM ITPG. The cellITPG. The cells were harvested by centrifugation as above and extracted in 10 mM phosphate buffer, pH 6.7, containing 1 mM EDTA, 0.1M PMSF, and 0.1 mcM pepstatin by sonication on ice for 15 sec using a microtip at power setting #3. After 15 min centrifugation in a Microfuge, the supernatant was collected and assayed for bioactivity in the ciliary ganglion survival assay (Example 1). There was substantial bioactivity in the supernatant (FIG. 22) which contained 1.5 mg/ml protein.

The results presented here indicate that two different DNA constructs in two different expression vectors allowed the expression of biologically active CNTF, which also migrated appropriately on reducing SDS polyacrylamide gels, was recognized by affinity-purified antibodies to CNTF, and had an appropriate amino-terminal amino acid sequence.

4. Purification of recombinant CNTF

A small inoculum of pT5T:CNTF-Syn1/3-5a is grown overnight at 37° C. with shaking in Luria broth containing 10 µg/ml of tetracycline. Seven ml of this cell suspension is added per 50 ml of Luria broth in large flasks and grown at 37° C. with shaking until the $A_{600}$ reaches approximately 0.5. Then, 0.5 mM final IPTG is added to induce expression of CNTF and growth continued until the $A_{600}$ reaches approximately 1.2 which typically takes 4–6 hrs. The cells are harvested by centrifugation JA-20 rotor at 7,000 rpm for 5 min at 4° C. and washed once more by centrifugation in 50 mM phosphate buffer, pH 8.0 (Buffer A) at 4° C. The supernatant is removed and the cell pellet is frozen at –20° C. as a paste.

The cell paste is suspended in Buffer B [Buffer A containing 1 mM EGTA (Ethylene Glycol-bis(-aminoethylEther) N,N,N',N'-Tetraacetic Acid) and 1 mM EDTA (Ethylenediaminetetraacetic Acid)] at 0.5 gm paste per ml buffer at 4° C. and passed three time through a French pressure cell to break open the bacteria. Polyethyleneimine (PEI) is added to a final concentration of 0.25% and shaken for 30 min at 4° C. The precipitate is removed by centrifugation for 15 min at top speed in a Microfuge. This step typically reduces the contents of nucleic acid, as measured by the ratio of $A_{260}/A_{280}$, from approximately 25% to less than 5%.

The sample is then applied to a column of Q-Sepharose (Pharmacia) equilibrated with Buffer B. CNTF is such a major component of the French pressed cell lysate that it can be followed during chromatography by Coomassie Brilliant Blue stained SDS-polyacrylamide gels of column fractions. CNTF is a major, Coomassie-stained band at approximately 24 kD. Using this assay, CNTF washes through the Q-Sepharose column in Buffer B.

The wash through fractions containing the bulk of CNTF protein are pooled, dialyzed against Buffer C (5 mM phosphate buffer, pH 8.0, containing 1 mM EGTA and 1 mM EDTA), and applied to a Q-Sepharose column equilibrated with Buffer C. The column is washed in Buffer C until the $A_{280}$ returns to baseline, indicating that non-adhering proteins have washed through the column. In Buffer C, CNTF binds to the Q-Sepharose column and is then eluted with a 0–0.1M NaCl gradient in Buffer C. CNTF emerges from the column at approximately 40 mM NaCl and is greater than 90% pure as judged on Coomassie stained SDS-polyacrylamide gels of the peak CNTF fractions.

What is claimed is:

1. Purified CNTF having the amino acid sequence set forth in FIG. 11.

2. Purified CNTF having the amino acid sequence set forth in FIG. 12.

3. Purified CNTF polypeptide prepared by the process of:
   (a) subcloning a purified and isolated nucleic acid molecule encoding the CNTF amino acid sequence set forth in FIG. 12 into an expression vector which comprises the regulatory elements needed to express the nucleic acid molecule;
   (b) transforming an *E. coli* host cell with said expression vector;
   (c) culturing the host cell under conditions for amplification of the vector and expression of the nucleic acid molecule; and
   (d) harvesting the CNTF polypeptide from the culture medium.

4. Purified CNTF prepared by the process of:
   (a) expressing in a host cell a nucleic acid encoding a CNTF polypeptide selected from the group consisting of amino acids 1–200 of FIG. 12 and amino acids 2–200 of FIG. 12; and
   (b) isolating the CNTF polypeptide.

5. The purified CNTF of claim 4 which has been produced in, and isolated from, an animal cell.

6. The purified CNTF of claim 4 which has been produced in, and isolated from, a bacterial cell.

7. The purified CNTF of claim 6 which has been produced in, and isolated from, an *E. coli* cell.

8. A purified CNTF polypeptide comprising amino acids 2–199 of FIG. 11.

9. A purified CNTF polypeptide comprising amino acids 2–200 of FIG. 12.

* * * * *

UNITED STATES PATENT AND TRADEMARK OFFICE
CERTIFICATE OF CORRECTION

PATENT NO.    : 5,780,600
DATED         : July 14, 1998
INVENTOR(S)   : Franklin D. Collins et al.

It is certified that error appears in the above-identified patent and that said Letters Patent is hereby corrected as shown below:

Column 2,
Line 39, change "substantially" to -- substantial --.

Column 3,
Line 39, change "advantageous" to -- preferred --.

Column 4,
Line 11, change "of" to -- on --.
Line 15, change "HPLC" to -- HIC --.

Column 6,
Line 57, change "products" to -- proteins --.

Column 7,
Line 44, change "activity" to -- activities --.

Column 8,
Line 28, change "there" to -- these --.

Column 9,
Line 37, change "Bold" to -- Gold --.

Column 10,
Line 6, change "completely" to -- completed --.
Line 26, change "Patterson" to -- Pettersson --.

Column 11,
Table 1, column 5, line 1, change "MHNA" to -- MRNA --.
Table 1, column 2, lines 4 and 5, between "(E. coli)", insert the word -- Tac --.
Table 1, column 6, line 6, delete the second use of "Factor".
Table 1, column 7, line 6, delete the second use of "Tap 1".

Column 15,
Line 62, change "has" to -- as --.

Column 17,
Line 41, change "which" to -- chick --.

Column 18,
Line 46, change "10 nM" to -- 10 mM --.
Line 47, change "1 nM" to -- 1 mM --.

UNITED STATES PATENT AND TRADEMARK OFFICE
CERTIFICATE OF CORRECTION

PATENT NO. : 5,780,600
DATED : July 14, 1998
INVENTOR(S) : Franklin D. Collins et al.

It is certified that error appears in the above-identified patent and that said Letters Patent is hereby corrected as shown below:

Column 19,
Line 30, change "nM" to -- mM --.

Column 21,
Line 67, after the word "vacuum", insert the word -- evaporator --.

Column 22,
Line 3, change "an" to -- and --.
Lines 30-32, change "L-A-R-K-I-R-S-D-L-T-E-S-Y-V-K-H-Q-G-L-N-K-N-I-N-L-D-S-V-D-G-V-P-M-A-" to -- L-A-R-K-I-R-S-D-L-T-A-L-T-E-S-Y-V-K-H-Q-G-L-N-K-N-I-N-L-D-S-V-D-G-V-P-M-A- --.

Column 25,
Line 35, change "ATF" to -- ATP --.
Line 45, change "rRNA" to -- tRNA --.

Column 27,
Line 12, change "4'" to -- 5' --.

Column 28,
Line 21, change "PCT" to -- PCR --.

Column 29,
Line 37, change "(SV4)" to -- (SV40) --.

Signed and Sealed this

Twenty-third Day of November, 2004

JON W. DUDAS
*Director of the United States Patent and Trademark Office*